(12) United States Patent
Cai et al.

(10) Patent No.: US 11,021,538 B2
(45) Date of Patent: *Jun. 1, 2021

(54) BISPECIFIC COUPLED ANTIBODY, PREPARATION METHOD AND APPLICATION THEREOF

(71) Applicant: SHANGHAI KANDA BIOTECHNOLOGY CO, LTD, Shanghai (CN)

(72) Inventors: Zeling Cai, Shanghai (CN); Yi Chen, Shanghai (CN)

( * ) Notice: Subject to any disclaimer, the term of this patent is extended or adjusted under 35 U.S.C. 154(b) by 288 days.

This patent is subject to a terminal disclaimer.

(21) Appl. No.: 16/011,565

(22) Filed: Jun. 18, 2018

(65) Prior Publication Data

US 2019/0048080 A1 Feb. 14, 2019

Related U.S. Application Data

(63) Continuation of application No. PCT/CN2016/110438, filed on Dec. 16, 2016.

(30) Foreign Application Priority Data

Dec. 16, 2015 (CN) .......................... 201510953199.4

(51) Int. Cl.
| | |
|---|---|
| *C07K 16/28* | (2006.01) |
| *C07K 16/30* | (2006.01) |
| *C07K 16/32* | (2006.01) |
| *A61P 35/00* | (2006.01) |
| *C07K 16/06* | (2006.01) |
| *C12N 15/62* | (2006.01) |
| *C12N 15/85* | (2006.01) |
| *C07K 16/46* | (2006.01) |

(52) U.S. Cl.
CPC .......... *C07K 16/2818* (2013.01); *A61P 35/00* (2018.01); *C07K 16/065* (2013.01); *C07K 16/3069* (2013.01); *C07K 16/32* (2013.01); *C12N 15/62* (2013.01); *C12N 15/85* (2013.01); *C07K 16/468* (2013.01); *C07K 2317/31* (2013.01); *C07K 2317/565* (2013.01); *C07K 2317/73* (2013.01); *C07K 2317/92* (2013.01)

(58) Field of Classification Search
CPC .................. C07K 16/2818; C07K 2317/31
See application file for complete search history.

(56) References Cited

U.S. PATENT DOCUMENTS

| | | | |
|---|---|---|---|
| 2002/0086012 A1* | 7/2002 | Wels | A61P 31/04 424/134.1 |
| 2013/0295121 A1 | 11/2013 | Johnson et al. | |
| 2014/0099254 A1 | 4/2014 | Chang et al. | |
| 2016/0362460 A1 | 12/2016 | Olwill et al. | |

FOREIGN PATENT DOCUMENTS

| | | |
|---|---|---|
| CN | 101052655 A | 10/2007 |
| CN | 102134276 A | 7/2011 |
| CN | 104292334 A | 1/2015 |
| CN | 104707136 A | 6/2015 |

OTHER PUBLICATIONS

Paul, Fundamental Immunology, 3rd Edition, 1993, pp. 292-295.*
Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
Rennerc. et al "Tumor Therapy by Immune Recruitment with Bispecific Antibodies" Immunological Reviews. No. 14531 Dec. 1995 (Dec. 31, 1995)pp. I79-209.
Biburgerm. et al "ANovel Bispecific Tetravalent Antibody Fusion Protein to Target Costimulatory Activity for T-cell Activation to Tumor Cells Overexpr ssing ErbB2/HER2" J. Mol.Biol.vol. 346No. 5Dec. 31, 2005 (Dec. 31, 2005)pp. 1299-1311.

\* cited by examiner

*Primary Examiner* — Hong Sang
(74) *Attorney, Agent, or Firm* — Erson IP (Nelson IP)

(57) ABSTRACT

A bispecific coupled antibody, a preparation method and an application thereof are provided. Specifically, an anti-CTLA-4 humanized single-chain antibody fragment (scFv) is provided, which has the advantages of high affinity and strong specificity. Using the anti-CTLA-4 antibody to construct a recombinant bispecific conjugated antibody (fusing a humanized anti-Her-2 full antibody (Trastuzumab) with anti-CTLA-4 human single-chain antibody (scFv, single-chain antibody fragment)) is capable of significantly enhancing the body's immune response and maintaining or enhancing the activation state of T cells.

5 Claims, 11 Drawing Sheets

Specification includes a Sequence Listing.

```
  1 - ATGGAGTTTGGTCTGTCCTGGCTGTTTCTGGTGGCTATCCTGAAGGGAGTGCAGTGCGAA  - 60
  1 - M  E  F  G  L  S  W  L  F  L  V  A  I  L  K  G  V  Q  C  E  - 20
 61 - GTGCAGCTGGTCGAATCTGGGGGAGGGCTGGTGCAGCCAGGAGGATCACTGAGGCTGTCC -120
 21 - V  Q  L  V  E  S  G  G  G  L  V  Q  P  G  G  S  L  R  L  S  - 40
121 - TGCGCCGCTAGCGGGTTCAACATCAAGGACACCTACATTCACTGGGTCAGACAGGCTCCT -180
 41 - C  A  A  S  G  F  N  I  K  D  T  Y  I  H  W  V  R  Q  A  P  - 60
181 - GGCAAGGGACTGGAGTGGGTGGCACGCATCTATCCAACTAATGGGTACACCAGATATGCC -240
 61 - G  K  G  L  E  W  V  A  R  I  Y  P  T  N  G  Y  T  R  Y  A  - 80
241 - GACTCTGTGAAGGGTCGGTTTACCATTTCTGCAGATACAAGTAAAAACACTGCCTACCTG -300
 81 - D  S  V  K  G  R  F  T  I  S  A  D  T  S  K  N  T  A  Y  L  -100
301 - CAGATGAACTCCCTGCGAGCCGAAGATACAGCCGTGTACTATTGCAGTCGTTGGGGGGGT -360
101 - Q  M  N  S  L  R  A  E  D  T  A  V  Y  Y  C  S  R  W  G  G  -120
361 - GACGGATTCTACGCTATGGATTATTGGGGCAGGGCACCCTGGTCACAGTGTCCAGCGCA  -420
121 - D  G  F  Y  A  M  D  Y  W  G  Q  G  T  L  V  T  V  S  S  A  -140
421 - TCAACAAAGGGGCCTTCCGTGTTTCCACTGGCCCCCTCTAGTAAAAGCACCTCTGGCGGA -480
141 - S  T  K  G  P  S  V  F  P  L  A  P  S  S  K  S  T  S  G  G  -160
481 - ACAGCAGCCCTGGGTTGTCTGGTGAAGGACTACTTCCCAGAGCCAGTCACCGTGTCCTGG -540
161 - T  A  A  L  G  C  L  V  K  D  Y  F  P  E  P  V  T  V  S  W  -180
541 - AACAGCGGCGCCCTGACATCCGGAGTCCATACTTTTCCTGCTGTGCTGCAGTCATCCGGG -600
181 - N  S  G  A  L  T  S  G  V  H  T  F  P  A  V  L  Q  S  S  G  -200
601 - CTGTACAGCCTGAGCTCTGTGGTCACTGTCCCAAGTTCATCCCTGGGTACTCAGACCTAT -660
201 - L  Y  S  L  S  S  V  V  T  V  P  S  S  S  L  G  T  Q  T  Y  -220
661 - ATCTGCAACGTGAATCACAAGCCATCCAATACCAAAGTGGACAAGAAAGTGGAGCCCAAG -720
221 - I  C  N  V  N  H  K  P  S  N  T  K  V  D  K  K  V  E  P  K  -240
721 - AGCTGTGATAAAACACATACTTGCCCCCCTTGTCCTGCACCAGAACTGCTGGGAGGTCCA -780
241 - S  C  D  K  T  H  T  C  P  P  C  P  A  P  E  L  L  G  G  P  -260
781 - TCCGTGTTCCTGTTTCCACCCAAGCCTAAAGACACCCTGATGATTTCTCGAACTCCAGAG -840
261 - S  V  F  L  F  P  P  K  P  K  D  T  L  M  I  S  R  T  P  E  -280
841 - GTCACCTGCGTGGTCGTGGACGTGTCCCACGAGGACCCCGAAGTCAAGTTCAACTGGTAC -900
281 - V  T  C  V  V  V  D  V  S  H  E  D  P  E  V  K  F  N  W  Y  -300
901 - GTGGATGGCGTCGAAGTGCATAATGCTAAGACAAAACCAAGAGAGGAACAGTACAACAGC -960
301 - V  D  G  V  E  V  H  N  A  K  T  K  P  R  E  E  Q  Y  N  S  -320
961 - ACTTATCGCGTCGTGTCTGTCCTGACCGTGCTGCACCAGGATTGGCTGAACGGCAAGGAG -1020
321 - T  Y  R  V  V  S  V  L  T  V  L  H  Q  D  W  L  N  G  K  E  -340
1021- TATAAGTGCAAAGTGAGCAATAAGGCTCTGCCCGCACCTATCGAGAAAACAATTTCTAAG -1080
341 - Y  K  C  K  V  S  N  K  A  L  P  A  P  I  E  K  T  I  S  K  -360
```

FIG. 2(A)

```
1081 - GCTAAAGGACAGCCTAGGGAACCACAGGTGTACACTCTGCCTCCATCTCGGGAGGAAATG -
1140
 361 - A  K  G  Q  P  R  E  P  Q  V  Y  T  L  P  P  S  R  E  E  M  - 380
1141 - ACCAAGAACCAGGTCAGTCTGACATGTCTGGTGAAAGGCTTCTATCCCTCCGACATCGCA -
1200
 381 - T  K  N  Q  V  S  L  T  C  L  V  K  G  F  Y  P  S  D  I  A  - 400
1201 - GTGGAGTGGGAAAGCAATGGACAGCCTGAGAACAATTACAAGACCACACCCCCTGTGCTG -
1260
 401 - V  E  W  E  S  N  G  Q  P  E  N  N  Y  K  T  T  P  P  V  L  - 420
1261 - GACTCTGATGGCAGTTTCTTTCTGTATAGTAAGCTGACCGTGGATAAATCACGGTGGCAG -
1320
 421 - D  S  D  G  S  F  F  L  Y  S  K  L  T  V  D  K  S  R  W  Q  - 440
1321 - CAGGGAAATGTCTTTAGTTGTTCAGTGATGCACGAAGCACTGCACAATCACTACACTCAG -
1380
 441 - Q  G  N  V  F  S  C  S  V  M  H  E  A  L  H  N  H  Y  T  Q  - 460
1381 - AAATCACTGTCACTGTCCCCAGGACAGGTCCAGCTGGTGCAGTCTGGGGGAGGCGTGGTC -
1440
 461 - K  S  L  S  L  S  P  G  Q  V  Q  L  V  Q  S  G  G  G  V  V  - 480
1441 - CAGCCTGGGAGGTCCCTGAGACTCTCCTGTGCAGCGTCTGGATTCACCTTCAGTAGCTAT -
1500
 481 - Q  P  G  R  S  L  R  L  S  C  A  A  S  G  F  T  F  S  S  Y  - 500
1501 - GGCATGCACTGGGTCCGCCAGGCTCCAGGCAAGGGGCTGGAGTGGGTGGCAGTTATATGG -
1560
 501 - G  M  H  W  V  R  Q  A  P  G  K  G  L  E  W  V  A  V  I  W  - 520
1561 - TATGATGGAAGTAGGCAATATTATGCTGACTCCGTGAAGGGCCGATTCACCATCTCCAGA -
1620
 521 - Y  D  G  S  R  Q  Y  Y  A  D  S  V  K  G  R  F  T  I  S  R  - 540
1621 - GACGATTCCAAGAACACGATGTATCTGCAAATGAACAGCCTGAGAGCCGAAGACACGGCT -
1680
 541 - D  D  S  K  N  T  M  Y  L  Q  M  N  S  L  R  A  E  D  T  A  - 560
1681 - GTTTATTACTGTGCGAGAGGGGGATTTTGGGGGGCTTTTGATATCTGGGGCCAAGGGACA -
1740
 561 - V  Y  Y  C  A  R  G  G  F  W  G  A  F  D  I  W  G  Q  G  T  - 580
1741 - ATGGTCACCGTCTCCTCAGGCAGCGGCGGTGGCGGATCCGATGTTGTGATGACTCAGTCT -
1800
 581 - M  V  T  V  S  S  G  S  G  G  G  G  S  D  V  V  M  T  Q  S  - 600
1801 - CCAGGCACCCTGTCTTTGTCTCCAGGGGAAGGAGCCACACTCTCCTGCAGGGCCAGTCAA -
1860
 601 - P  G  T  L  S  L  S  P  G  E  G  A  T  L  S  C  R  A  S  Q  - 620
1861 - CATGTTATCAGCAGCTACTTAGCCTGGTATCAGCAAAAACCTGGCCAGGCTCCCAGGCTC -
1920
 621 - H  V  I  S  S  Y  L  A  W  Y  Q  Q  K  P  G  Q  A  P  R  L  - 640
1921 - CTCGTCTACGGTGCATCCAGTAGGGACACTGGCGTCTCAGACAGGTTCACTGGCAGTGGG -
1980
 641 - L  V  Y  G  A  S  S  R  D  T  G  V  S  D  R  F  T  G  S  G  - 660
1981 - TCTGGGACAGACTTCACTCTCACCATCAGCAGACTGGAGCCTGAAGATTCTGCGGTGTAT -
2040
 661 - S  G  T  D  F  T  L  T  I  S  R  L  E  P  E  D  S  A  V  Y  - 680
2041 - TTCTGTCAGCAGTATGGTACATCACCGTGGACGTTCGGCCAAGGGACCAAGCTGGAGATC -
2100
 681 - F  C  Q  Q  Y  G  T  S  P  W  T  F  G  Q  G  T  K  L  E  I  - 700
2101 - AAACGTTAA - 2109
 701 - K  R                                                          - 720
```

FIG. 2(A)- Continued

```
  1 - ATGCGTGTGCCTGCTCAGCTGCTGGGTCTGCTGCTGCTGTGGCTGCGTGGGGCTCGTTGT -  60
  1 - M  R  V  P  A  Q  L  L  G  L  L  L  L  W  L  R  G  A  R  C  - 20
 61 - GACATTCAGATGACTCAGTCTCCTTCATCACTGTCCGCTAGCGTGGGCGACAGAGTCACT - 120
 21 - D  I  Q  M  T  Q  S  P  S  S  L  S  A  S  V  G  D  R  V  T  - 40
121 - ATCACCTGCCGCGCATCCCAGGATGTGAACACCGCAGTCGCCTGGTATCAGCAGAAGCCT - 180
 41 - I  T  C  R  A  S  Q  D  V  N  T  A  V  A  W  Y  Q  Q  K  P  - 60
181 - GGCAAAGCTCCAAAGCTGCTGATCTACTCTGCAAGTTTCCTGTATAGTGGAGTGCCCTCA - 240
 61 - G  K  A  P  K  L  L  I  Y  S  A  S  F  L  Y  S  G  V  P  S  - 80
241 - AGGTTTTCAGGGTCCCGGAGCGGCACCGACTTCACACTGACTATCTCCAGCCTGCAGCCT - 300
 81 - R  F  S  G  S  R  S  G  T  D  F  T  L  T  I  S  S  L  Q  P  - 100
301 - GAGGATTTTGCCACATACTATTGCCAGCAGCACTATACCACACCCCCTACTTTCGGCCAG - 360
101 - E  D  F  A  T  Y  Y  C  Q  Q  H  Y  T  T  P  P  T  F  G  Q  - 120
361 - GGAACCAAAGTGGAGATCAAGCGAACTGTGGCCGCTCCATCTGTCTTCATTTTTCCACCC - 420
121 - G  T  K  V  E  I  K  R  T  V  A  A  P  S  V  F  I  F  P  P  - 140
421 - AGTGACGAACAGCTGAAGTCCGGGACAGCTAGCGTGGTCTGTCTGCTGAACAATTTTTAC - 480
141 - S  D  E  Q  L  K  S  G  T  A  S  V  V  C  L  L  N  N  F  Y  - 160
481 - CCCAGGGAAGCCAAAGTGCAGTGGAAGGTCGATAACGCTCTGCAGTCTGGAAATAGTCAG - 540
161 - P  R  E  A  K  V  Q  W  K  V  D  N  A  L  Q  S  G  N  S  Q  - 180
541 - GAGTCAGTGACAGAACAGGACTCCAAAGATAGCACTTATTCTCTGTCTAGTACCCTGACA - 600
181 - E  S  V  T  E  Q  D  S  K  D  S  T  Y  S  L  S  S  T  L  T  - 200
601 - CTGAGCAAGGCAGACTACGAGAAGCATAAAGTGTATGCCTGTGAAGTCACTCATCAGGGG - 660
201 - L  S  K  A  D  Y  E  K  H  K  V  Y  A  C  E  V  T  H  Q  G  - 220
661 - CTGTCCAGTCCCGTCACAAAATCCTTTAATCGTGGCGAATGTTGA - 705
221 - L  S  S  P  V  T  K  S  F  N  R  G  E  C              - 240
```

FIG. 2(B)

```
                        SEQUENCE LISTING

<160> NUMBER OF SEQ ID NOS: 40

<210> SEQ ID NO 1
<211> LENGTH: 126
<212> TYPE: PRT
<213> ORGANISM: Homo sapiens

<400> SEQUENCE: 1

Ala Met His Val Ala Gln Pro Ala Val Val Leu Ala Ser Ser Arg Gly
1               5                   10                  15

Ile Ala Ser Phe Val Cys Glu Tyr Ala Ser Pro Gly Lys Ala Thr Glu
                20                  25                  30

Val Arg Val Thr Val Leu Arg Gln Ala Asp Ser Gln Val Thr Glu Val
            35                  40                  45

Cys Ala Ala Thr Tyr Met Met Gly Asn Glu Leu Thr Phe Leu Asp Asp
        50                  55                  60

Ser Ile Cys Thr Gly Thr Ser Ser Gly Asn Gln Val Asn Leu Thr Ile
65                  70                  75                  80

Gln Gly Leu Arg Ala Met Asp Thr Gly Leu Tyr Ile Cys Lys Val Glu
                85                  90                  95

Leu Met Tyr Pro Pro Pro Tyr Tyr Leu Gly Ile Gly Asn Gly Thr Gln
                100                 105                 110

Ile Tyr Val Ile Asp Pro Glu Pro Cys Pro Asp Ser Asp Phe
            115                 120                 125

<210> SEQ ID NO 2
<211> LENGTH: 630
<212> TYPE: PRT
<213> ORGANISM: Homo sapiens

<400> SEQUENCE: 2

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
                20                  25                  30

Val Val Gln Gly Asn Leu Glu Leu Thr Tyr Leu Pro Thr Asn Ala Ser
            35                  40                  45

Leu Ser Phe Leu Gln Asp Ile Gln Glu Val Gln Gly Tyr Val Leu Ile
        50                  55                  60
```

-continued

```
Ala His Asn Gln Val Arg Gln Val Pro Leu Gln Arg Leu Arg Ile Val
 65                  70                  75                  80

Arg Gly Thr Gln Leu Phe Glu Asp Asn Tyr Ala Leu Ala Val Leu Asp
                 85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
```

His Cys Trp Gly Pro Gly Pro Thr Gln Cys Val Asn Cys Ser Gln Phe
                500                 505                 510

Leu Arg Gly Gln Glu Cys Val Glu Glu Cys Arg Val Leu Gln Gly Leu
            515                 520                 525

Pro Arg Glu Tyr Val Asn Ala Arg His Cys Leu Pro Cys His Pro Glu
        530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Gly Ala Cys Gln Pro Cys Pro Ile Asn Cys
        595                 600                 605

Thr His Ser Cys Val Asp Leu Asp Asp Lys Gly Cys Pro Ala Glu Gln
        610                 615                 620

Arg Ala Ser Pro Leu Thr
625                 630

<210> SEQ ID NO 3
<211> LENGTH: 354
<212> TYPE: DNA
<213> ORGANISM: Artificial Sequence
<220> FEATURE:
<223> OTHER INFORMATION: synthetic

<400> SEQUENCE: 3
caggtccagc tggtgcagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg gtggcagtt atatggtatg atggaagtag caatattat      180 gctgactccg tgaagggccg attcaccatc tccagagacg attccaagaa cacgatgtat     240
ctgcaaatga acagcctgag agccgaagac acggctgttt attactgtgc gagagggga      300 ttttgggggg cttttgatat ctggggccaa gggacaatgg tcaccgtctc ctca           354

<210> SEQ ID NO 4
<211> LENGTH: 118
<212> TYPE: PRT
<213> ORGANISM: Artificial Sequence
<220> FEATURE:
<223> OTHER INFORMATION: synthetic

<400> SEQUENCE: 4

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Arg Gln Tyr Tyr Ala Asp Ser Val
    50                  55                  60

Lys Gly Arg Phe Thr Ile Ser Arg Asp Asp Ser Lys Asn Thr Met Tyr
65                  70                  75                  80

Leu Gln Met Asn Ser Leu Arg Ala Glu Asp Thr Ala Val Tyr Tyr Cys
            85                  90                  95

Ala Arg Gly Gly Phe Trp Gly Ala Phe Asp Ile Trp Gly Gln Gly Thr
            100                 105                 110

Met Val Thr Val Ser Ser
        115

<210> SEQ ID NO 5
<211> LENGTH: 5
<212> TYPE: PRT
<213> ORGANISM: Artificial Sequence
<220> FEATURE:
<223> OTHER INFORMATION: synthetic

<400> SEQUENCE: 5

Ser Tyr Gly Met His
1               5

<210> SEQ ID NO 6
<211> LENGTH: 14
<212> TYPE: PRT
<213> ORGANISM: Artificial Sequence
<220> FEATURE:
<223> OTHER INFORMATION: synthetic

<400> SEQUENCE: 6

Val Ile Trp Tyr Asp Gly Ser Arg Gln Tyr Tyr Ala Asp Ser
1               5                   10

<210> SEQ ID NO 7
<211> LENGTH: 9
<212> TYPE: PRT
<213> ORGANISM: Artificial Sequence
<220> FEATURE:
<223> OTHER INFORMATION: synthetic

<400> SEQUENCE: 7

Gly Gly Phe Trp Gly Ala Phe Asp Ile
1               5

<210> SEQ ID NO 8
<211> LENGTH: 7
<212> TYPE: PRT
<213> ORGANISM: Artificial Sequence
<220> FEATURE:
<223> OTHER INFORMATION: synthetic

<400> SEQUENCE: 8

Gly Ser Gly Gly Gly Gly Ser
1               5

<210> SEQ ID NO 9
<211> LENGTH: 327
<212> TYPE: DNA
<213> ORGANISM: Artificial Sequence
<220> FEATURE:
<223> OTHER INFORMATION: synthetic

<400> SEQUENCE: 9
gatgttgtga tgactcagtc tccaggcacc ctgtctttgt ctccagggga aggagccaca      60
ctctcctgca gggccagtca acatgttatc agcagctact tagcctggta tcagcaaaaa     120
cctggccagg ctcccaggct cctcgtctac ggtgcatcca gtagggacac tggcgtctca     180
gacaggttca ctggcagtgg gtctgggaca gacttcactc tcaccatcag cagactggag     240
cctgaagatt ctgcggtgta tttctgtcag cagtatggta catcaccgtg gacgttcggc     300
caagggacca agctggagat caaacgt                                         327

```
<210> SEQ ID NO 10
<211> LENGTH: 109
<212> TYPE: PRT
<213> ORGANISM: Artificial Sequence
<220> FEATURE:
<223> OTHER INFORMATION: synthetic

<400> SEQUENCE: 10

Asp Val Val Met Thr Gln Ser Pro Gly Thr Leu Ser Leu Ser Pro Gly
1               5                   10                  15

Glu Gly Ala Thr Leu Ser Cys Arg Ala Ser Gln His Val Ile Ser Ser
            20                  25                  30

Tyr Leu Ala Trp Tyr Gln Gln Lys Pro Gly Gln Ala Pro Arg Leu Leu
        35                  40                  45

Val Tyr Gly Ala Ser Ser Arg Asp Thr Gly Val Ser Asp Arg Phe Thr
    50                  55                  60

Gly Ser Gly Ser Gly Thr Asp Phe Thr Leu Thr Ile Ser Arg Leu Glu
65                  70                  75                  80

Pro Glu Asp Ser Ala Val Tyr Phe Cys Gln Gln Tyr Gly Thr Ser Pro
                85                  90                  95

Trp Thr Phe Gly Gln Gly Thr Lys Leu Glu Ile Lys Arg
            100                 105

<210> SEQ ID NO 11
<211> LENGTH: 12
<212> TYPE: PRT
<213> ORGANISM: Artificial Sequence
<220> FEATURE:
<223> OTHER INFORMATION: synthetic

<400> SEQUENCE: 11

Arg Ala Ser Gln His Val Ile Ser Ser Tyr Leu Ala
1               5                   10

<210> SEQ ID NO 12
<211> LENGTH: 7
<212> TYPE: PRT
<213> ORGANISM: Artificial Sequence
<220> FEATURE:
<223> OTHER INFORMATION: synthetic

<400> SEQUENCE: 12

Gly Ala Ser Ser Arg Asp Thr
1               5

<210> SEQ ID NO 13
<211> LENGTH: 10
<212> TYPE: PRT
<213> ORGANISM: Artificial Sequence
<220> FEATURE:
<223> OTHER INFORMATION: synthetic

<400> SEQUENCE: 13

Gln Gln Tyr Gly Thr Ser Pro Trp Thr Phe
1               5                   10

<210> SEQ ID NO 14
<211> LENGTH: 1347
<212> TYPE: DNA
<213> ORGANISM: Artificial Sequence
<220> FEATURE:
<223> OTHER INFORMATION: synthetic
```

<400> SEQUENCE: 14

```
gaagtgcagc tggtcgaatc tgggggaggg ctggtgcagc caggaggatc actgaggctg      60
tcctgcgccg ctagcgggtt caacatcaag gacacctaca ttcactgggt cagacaggct     120
cctggcaagg gactggagtg ggtggcacgc atctatccaa ctaatgggta caccagatat     180
gccgactctg tgaagggtcg gtttaccatt tctgcagata caagtaaaaa cactgcctac     240
ctgcagatga actccctgcg agccgaagat acagccgtgt actattgcag tcgttggggg     300
ggtgacggat tctacgctat ggattattgg gggcagggca ccctggtcac agtgtccagc     360
gcatcaacaa agggccttc cgtgtttcca ctggcccct ctagtaaaag cacctctggc     420
ggaacagcag ccctgggttg tctggtgaag gactacttcc cagagccagt caccgtgtcc     480
tggaacagcg gcgccctgac atccggagtc catactttc ctgctgtgct gcagtcatcc     540
gggctgtaca gcctgagctc tgtggtcact gtcccaagtt catccctggg tactcagacc     600
tatatctgca acgtgaatca caagccatcc aataccaaag tggacaagaa agtggagccc     660
aagagctgtg ataaaacaca tacttgcccc ccttgtcctg caccagaact gctgggaggt     720
ccatccgtgt tcctgtttcc acccaagcct aaagacaccc tgatgatttc tcgaactcca     780
gaggtcacct gcgtggtcgt ggacgtgtcc acgaggacc ccgaagtcaa gttcaactgg     840
tacgtggatg gcgtcgaagt gcataatgct aagacaaaac caagagagga cagtacaac     900
agcacttatc gcgtcgtgtc tgtcctgacc gtgctgcacc aggattggct gaacggcaag     960
gagtataagt gcaaagtgag caataaggct ctgcccgcac ctatcgagaa aacaatttct    1020
aaggctaaag gacagcctag ggaaccacag gtgtacactc tgcctccatc tcgggaggaa    1080
atgaccaaga accaggtcag tctgacatgt ctggtgaaag gcttctatcc ctccgacatc    1140
gcagtggagt gggaaagcaa tggacagcct gagaacaatt acaagaccac cccctgtg    1200
ctggactctg atggcagttt cttctgtat agtaagctga ccgtggataa atcacggtgg    1260
cagcagggaa atgtctttag ttgttcagtg atgcacgaag cactgcacaa tcactacact    1320
cagaaatcac tgtcactgtc cccagga                                         1347
```

<210> SEQ ID NO 15
<211> LENGTH: 449
<212> TYPE: PRT
<213> ORGANISM: Artificial Sequence
<220> FEATURE:
<223> OTHER INFORMATION: synthetic

<400> SEQUENCE: 15

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110
```

Gly Thr Leu Val Thr Val Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 16
<211> LENGTH: 642
<212> TYPE: DNA
<213> ORGANISM: Artificial Sequence
<220> FEATURE:
<223> OTHER INFORMATION: synthetic

<400> SEQUENCE: 16
gacattcaga tgactcagtc tccttcatca ctgtccgcta gcgtgggcga cagagtcact        60
atcacctgcc gcgcatccca ggatgtgaac accgcagtcg cctggtatca gcagaagcct       120

```
ggcaaagctc caaagctgct gatctactct gcaagtttcc tgtatagtgg agtgccctca    180
aggttttcag ggtcccggag cggcaccgac ttcacactga ctatctccag cctgcagcct    240
gaggattttg ccacatacta ttgccagcag cactatacca caccccctac tttcggccag    300
ggaaccaaag tggagatcaa gcgaactgtg ccgctccat ctgtcttcat ttttccaccc     360
agtgacgaac agctgaagtc cggacagct agcgtggtct gtctgctgaa caatttttac     420
cccagggaag ccaaagtgca gtggaaggtc gataacgctc tgcagtctgg aaatagtcag    480
gagtcagtga cagaacagga ctccaaagat agcacttatt ctctgtctag taccctgaca    540
ctgagcaagg cagactacga gaagcataaa gtgtatgcct gtgaagtcac tcatcagggg    600
ctgtccagtc ccgtcacaaa atcctttaat cgtggcgaat gt                       642
```

<210> SEQ ID NO 17
<211> LENGTH: 214
<212> TYPE: PRT
<213> ORGANISM: Artificial Sequence
<220> FEATURE:
<223> OTHER INFORMATION: synthetic

<400> SEQUENCE: 17

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 18
<211> LENGTH: 8
<212> TYPE: PRT
<213> ORGANISM: Artificial Sequence
<220> FEATURE:
<223> OTHER INFORMATION: synthetic

<400> SEQUENCE: 18

```
Gly Phe Asn Ile Lys Asp Thr Tyr
1               5

<210> SEQ ID NO 19
<211> LENGTH: 8
<212> TYPE: PRT
<213> ORGANISM: Artificial Sequence
<220> FEATURE:
<223> OTHER INFORMATION: synthetic

<400> SEQUENCE: 19

Ile Tyr Pro Thr Asn Gly Tyr Thr
1               5

<210> SEQ ID NO 20
<211> LENGTH: 13
<212> TYPE: PRT
<213> ORGANISM: Artificial Sequence
<220> FEATURE:
<223> OTHER INFORMATION: synthetic

<400> SEQUENCE: 20

Ser Arg Trp Gly Gly Asp Gly Phe Tyr Ala Met Asp Tyr
1               5                   10

<210> SEQ ID NO 21
<211> LENGTH: 6
<212> TYPE: PRT
<213> ORGANISM: Artificial Sequence
<220> FEATURE:
<223> OTHER INFORMATION: synthetic

<400> SEQUENCE: 21

Gln Asp Val Asn Thr Ala
1               5

<210> SEQ ID NO 22
<211> LENGTH: 7
<212> TYPE: PRT
<213> ORGANISM: Artificial Sequence
<220> FEATURE:
<223> OTHER INFORMATION: synthetic

<400> SEQUENCE: 22

Ser Ala Ser Phe Leu Tyr Ser
1               5

<210> SEQ ID NO 23
<211> LENGTH: 9
<212> TYPE: PRT
<213> ORGANISM: Artificial Sequence
<220> FEATURE:
<223> OTHER INFORMATION: synthetic

<400> SEQUENCE: 23

Gln Gln His Tyr Thr Thr Pro Pro Thr
1               5

<210> SEQ ID NO 24
<211> LENGTH: 234
<212> TYPE: PRT
<213> ORGANISM: Artificial Sequence
<220> FEATURE:
<223> OTHER INFORMATION: synthetic

<400> SEQUENCE: 24
```

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Arg Gln Tyr Tyr Ala Asp Ser Val
    50                  55                  60

Lys Gly Arg Phe Thr Ile Ser Arg Asp Asp Ser Lys Asn Thr Met Tyr
65                  70                  75                  80

Leu Gln Met Asn Ser Leu Arg Ala Glu Asp Thr Ala Val Tyr Tyr Cys
                85                  90                  95

Ala Arg Gly Gly Phe Trp Gly Ala Phe Asp Ile Trp Gly Gln Gly Thr
            100                 105                 110

Met Val Thr Val Ser Ser Gly Ser Gly Gly Gly Ser Asp Val Val
        115                 120                 125

Met Thr Gln Ser Pro Gly Thr Leu Ser Leu Ser Pro Gly Glu Gly Ala
        130                 135                 140

Thr Leu Ser Cys Arg Ala Ser Gln His Val Ile Ser Ser Tyr Leu Ala
145                 150                 155                 160

Trp Tyr Gln Gln Lys Pro Gly Gln Ala Pro Arg Leu Leu Val Tyr Gly
                165                 170                 175

Ala Ser Ser Arg Asp Thr Gly Val Ser Asp Arg Phe Thr Gly Ser Gly
            180                 185                 190

Ser Gly Thr Asp Phe Thr Leu Thr Ile Ser Arg Leu Glu Pro Glu Asp
        195                 200                 205

Ser Ala Val Tyr Phe Cys Gln Gln Tyr Gly Thr Ser Pro Trp Thr Phe
    210                 215                 220

Gly Gln Gly Thr Lys Leu Glu Ile Lys Arg
225                 230

<210> SEQ ID NO 25
<211> LENGTH: 30
<212> TYPE: PRT
<213> ORGANISM: Artificial Sequence
<220> FEATURE:
<223> OTHER INFORMATION: synthetic

<400> SEQUENCE: 25

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 26
<211> LENGTH: 14
<212> TYPE: PRT
<213> ORGANISM: Artificial Sequence
<220> FEATURE:
<223> OTHER INFORMATION: synthetic

<400> SEQUENCE: 26

Trp Val Arg Gln Ala Pro Gly Lys Gly Leu Glu Trp Val Ala
1               5                   10

<210> SEQ ID NO 27
<211> LENGTH: 35
<212> TYPE: PRT
<213> ORGANISM: Artificial Sequence
<220> FEATURE:
<223> OTHER INFORMATION: synthetic

<400> SEQUENCE: 27

Val Lys Gly Arg Phe Thr Ile Ser Arg Asp Asp Ser Lys Asn Thr Met
1               5                   10                  15

Tyr Leu Gln Met Asn Ser Leu Arg Ala Glu Asp Thr Ala Val Tyr Tyr
                20                  25                  30

Cys Ala Arg
        35

<210> SEQ ID NO 28
<211> LENGTH: 11
<212> TYPE: PRT
<213> ORGANISM: Artificial Sequence
<220> FEATURE:
<223> OTHER INFORMATION: synthetic

<400> SEQUENCE: 28

Trp Gly Gln Gly Thr Met Val Thr Val Ser Ser
1               5                   10

<210> SEQ ID NO 29
<211> LENGTH: 23
<212> TYPE: PRT
<213> ORGANISM: Artificial Sequence
<220> FEATURE:
<223> OTHER INFORMATION: synthetic

<400> SEQUENCE: 29

Asp Val Val Met Thr Gln Ser Pro Gly Thr Leu Ser Leu Ser Pro Gly
1               5                   10                  15

Glu Gly Ala Thr Leu Ser Cys
            20

<210> SEQ ID NO 30
<211> LENGTH: 15
<212> TYPE: PRT
<213> ORGANISM: Artificial Sequence
<220> FEATURE:
<223> OTHER INFORMATION: synthetic

<400> SEQUENCE: 30

Trp Tyr Gln Gln Lys Pro Gly Gln Ala Pro Arg Leu Leu Val Tyr
1               5                   10                  15

<210> SEQ ID NO 31
<211> LENGTH: 32
<212> TYPE: PRT
<213> ORGANISM: Artificial Sequence
<220> FEATURE:
<223> OTHER INFORMATION: synthetic

<400> SEQUENCE: 31

Gly Val Ser Asp Arg Phe Thr Gly Ser Gly Ser Gly Thr Asp Phe Thr
1               5                   10                  15

Leu Thr Ile Ser Arg Leu Glu Pro Glu Asp Ser Ala Val Tyr Phe Cys
                20                  25                  30

<210> SEQ ID NO 32
<211> LENGTH: 10
<212> TYPE: PRT
<213> ORGANISM: Artificial Sequence
<220> FEATURE:
<223> OTHER INFORMATION: synthetic -continued

<400> SEQUENCE: 32

Gly Gln Gly Thr Lys Leu Glu Ile Lys Arg
1               5                   10

<210> SEQ ID NO 33
<211> LENGTH: 28
<212> TYPE: DNA
<213> ORGANISM: Artificial Sequence
<220> FEATURE:
<223> OTHER INFORMATION: synthetic

<400> SEQUENCE: 33
attgaattcc gcggccgcca ccatggag                                          28

<210> SEQ ID NO 34
<211> LENGTH: 20
<212> TYPE: DNA
<213> ORGANISM: Artificial Sequence
<220> FEATURE:
<223> OTHER INFORMATION: synthetic

<400> SEQUENCE: 34
tcctggggac agtgacagtg                                                   20

<210> SEQ ID NO 35
<211> LENGTH: 40
<212> TYPE: DNA
<213> ORGANISM: Artificial Sequence
<220> FEATURE:
<223> OTHER INFORMATION: synthetic

<400> SEQUENCE: 35
cactgtcact gtccccagga caggtccagc tggtgcagtc                             40

<210> SEQ ID NO 36
<211> LENGTH: 41
<212> TYPE: PRT
<213> ORGANISM: Artificial Sequence
<220> FEATURE:
<223> OTHER INFORMATION: synthetic

<400> SEQUENCE: 36

Ala Gly Ala Ala Thr Ala Gly Gly Gly Cys Cys Cys Thr Cys Thr Ala
1               5                   10                  15

Gly Ala Thr Thr Ala Ala Cys Gly Thr Thr Gly Ala Thr Cys Thr
            20                  25                  30

Cys Cys Ala Gly Cys Thr Thr Gly Gly
        35                  40

<210> SEQ ID NO 37
<211> LENGTH: 2109
<212> TYPE: DNA
<213> ORGANISM: Artificial Sequence
<220> FEATURE:
<223> OTHER INFORMATION: synthetic

<400> SEQUENCE: 37
atggagtttg gtctgtcctg gctgtttctg gtggctatcc tgaagggagt gcagtgcgaa       60
gtgcagctgg tcgaatctgg gggagggctg gtgcagccag gaggatcact gaggctgtcc      120
tgcgccgcta gcgggttcaa catcaaggac acctacattc actgggtcag acaggctcct      180
ggcaagggac tggagtgggt ggcacgcatc tatccaacta tgggtacac cagatatgcc       240

```
gactctgtga agggtcggtt taccatttct gcagatacaa gtaaaaacac tgcctacctg    300
cagatgaact ccctgcgagc cgaagataca gccgtgtact attgcagtcg ttggggggt     360 gacggattct acgctatgga ttattggggg cagggcaccc tggtcacagt gtccagcgca    420
tcaacaaagg ggccttccgt gtttccactg gcccctcta gtaaaagcac ctctggcgga    480
acagcagccc tgggttgtct ggtgaaggac tacttcccag agccagtcac cgtgtcctgg    540
aacagcggcg ccctgacatc cggagtccat acttttcctg ctgtgctgca gtcatccggg    600
ctgtacagcc tgagctctgt ggtcactgtc ccaagttcat ccctgggtac tcagacctat    660
atctgcaacg tgaatcacaa gccatccaat accaaagtgg acaagaaagt ggagcccaag    720
agctgtgata aaacacatac ttgcccccct tgtcctgcac agaactgct gggaggtcca    780 tccgtgttcc tgtttccacc caagcctaaa gacaccctga tgatttctcg aactccagag    840
gtcacctgcg tggtcgtgga cgtgtcccac gaggaccccg aagtcaagtt caactggtac    900
gtggatggcg tcgaagtgca taatgctaag acaaaaccaa gagaggaaca gtacaacagc    960
acttatcgcg tcgtgtctgt cctgaccgtg ctgcaccagg attggctgaa cggcaaggag    1020
tataagtgca agtgagcaa taaggctctg cccgcaccta tcgagaaaac aatttctaag    1080
gctaaaggac agcctaggga accacaggtg tacactctgc ctccatctcg ggaggaaatg    1140
accaagaacc aggtcagtct gacatgtctg gtgaaaggct tctatccctc cgacatcgca    1200
gtggagtggg aaagcaatgg acagcctgag acaattaca agaccacacc ccctgtgctg    1260
gactctgatg gcagtttctt tctgtatagt aagctgaccg tggataaatc acggtggcag    1320
cagggaaatg tctttagttg ttcagtgatg cacgaagcac tgcacaatca ctacactcag    1380
aaatcactgt cactgtcccc aggacaggtc cagctggtgc agtctggggg aggcgtggtc    1440
cagcctggga ggtccctgag actctcctgt gcagcgtctg gattcacctt cagtagctat    1500
ggcatgcact gggtccgcca ggctccaggc aaggggctgg agtgggtggc agttatatgg    1560
tatgatggaa gtaggcaata ttatgctgac tccgtgaagg gccgattcac catctccaga    1620
gacgattcca agaacacgat gtatctgcaa atgaacagcc tgagagccga agacacggct    1680
gtttattact gtgcgagagg gggattttgg ggggcttttg atatctgggg ccaagggaca    1740
atggtcaccg tctcctcagg cagcggcggt ggcggatccg atgttgtgat gactcagtct    1800
ccaggcaccc tgtctttgtc tccaggggaa ggagccacac tctcctgcag ggccagtcaa    1860
catgttatca gcagctactt agcctggtat cagcaaaaac ctggccaggc tcccaggctc    1920
ctcgtctacg gtgcatccag tagggacact ggcgtctcag acaggttcac tggcagtggg    1980
tctgggacag acttcactct caccatcagc agactggagc ctgaagattc tgcggtgtat    2040
ttctgtcagc agtatggtac atcaccgtgg acgttcggcc aagggaccaa gctggagatc    2100
aaacgttaa                                                           2109
```

<210> SEQ ID NO 38
<211> LENGTH: 702
<212> TYPE: PRT
<213> ORGANISM: Artificial Sequence
<220> FEATURE:
<223> OTHER INFORMATION: synthetic

<400> SEQUENCE: 38

Met Glu Phe Gly Leu Ser Trp Leu Phe Leu Val Ala Ile Leu Lys Gly
1               5                   10                  15

Val Gln Cys Glu Val Gln Leu Val Glu Ser Gly Gly Gly Leu Val Gln
            20                  25                  30

```
Pro Gly Gly Ser Leu Arg Leu Ser Cys Ala Ala Ser Gly Phe Asn Ile
            35                  40                  45

Lys Asp Thr Tyr Ile His Trp Val Arg Gln Ala Pro Gly Lys Gly Leu
 50                      55                  60

Glu Trp Val Ala Arg Ile Tyr Pro Thr Asn Gly Tyr Thr Arg Tyr Ala
 65                  70                  75                  80

Asp Ser Val Lys Gly Arg Phe Thr Ile Ser Ala Asp Thr Ser Lys Asn
                 85                  90                  95

Thr Ala Tyr Leu Gln Met Asn Ser Leu Arg Ala Glu Asp Thr Ala Val
            100                 105                 110

Tyr Tyr Cys Ser Arg Trp Gly Asp Gly Phe Tyr Ala Met Asp Tyr
            115                 120                 125

Trp Gly Gln Gly Thr Leu Val Thr Val Ser Ser Ala Ser Thr Lys Gly
            130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
                195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445
```

```
Val Met His Glu Ala Leu His Asn His Tyr Thr Gln Lys Ser Leu Ser
    450                 455                 460
Leu Ser Pro Gly Gln Val Gln Leu Val Gln Ser Gly Gly Gly Val Val
465                 470                 475                 480
Gln Pro Gly Arg Ser Leu Arg Leu Ser Cys Ala Ala Ser Gly Phe Thr
                485                 490                 495
Phe Ser Ser Tyr Gly Met His Trp Val Arg Gln Ala Pro Gly Lys Gly
                500                 505                 510
Leu Glu Trp Val Ala Val Ile Trp Tyr Asp Gly Ser Arg Gln Tyr Tyr
            515                 520                 525
Ala Asp Ser Val Lys Gly Arg Phe Thr Ile Ser Arg Asp Asp Ser Lys
    530                 535                 540
Asn Thr Met Tyr Leu Gln Met Asn Ser Leu Arg Ala Glu Asp Thr Ala
545                 550                 555                 560
Val Tyr Tyr Cys Ala Arg Gly Gly Phe Trp Gly Ala Phe Asp Ile Trp
                565                 570                 575
Gly Gln Gly Thr Met Val Thr Val Ser Ser Gly Ser Gly Gly Gly Gly
                580                 585                 590
Ser Asp Val Val Met Thr Gln Ser Pro Gly Thr Leu Ser Leu Ser Pro
            595                 600                 605
Gly Glu Gly Ala Thr Leu Ser Cys Arg Ala Ser Gln His Val Ile Ser
    610                 615                 620
Ser Tyr Leu Ala Trp Tyr Gln Gln Lys Pro Gly Gln Ala Pro Arg Leu
625                 630                 635                 640
Leu Val Tyr Gly Ala Ser Ser Arg Asp Thr Gly Val Ser Asp Arg Phe
                645                 650                 655
Thr Gly Ser Gly Ser Gly Thr Asp Phe Thr Leu Thr Ile Ser Arg Leu
                660                 665                 670
Glu Pro Glu Asp Ser Ala Val Tyr Phe Cys Gln Gln Tyr Gly Thr Ser
            675                 680                 685
Pro Trp Thr Phe Gly Gln Gly Thr Lys Leu Glu Ile Lys Arg
    690                 695                 700

<210> SEQ ID NO 39
<211> LENGTH: 705
<212> TYPE: DNA
<213> ORGANISM: Artificial Sequence
<220> FEATURE:
<223> OTHER INFORMATION: synthetic

<400> SEQUENCE: 39
atgcgtgtgc tgctcagct gctgggtctg ctgctgctgt ggctgcgtgg ggctcgttgt        60
gacattcaga tgactcagtc tccttcatca ctgtccgcta gcgtgggcga cagagtcact       120
atcacctgcc gcgcatccca ggatgtgaac accgcagtcg cctggtatca gcagaagcct       180
ggcaaagctc caaagctgct gatctactct gcaagtttcc tgtatagtgg agtgccctca       240
aggttttcag gtcccggag cggcaccgac ttcacactga ctatctccag cctgcagcct       300
gaggattttg ccacatacta ttgccagcag cactatacca cccccctac tttcggccag       360 ggaaccaaag tggagatcaa gcgaactgtg gccgctccat ctgtcttcat ttttccaccc       420
agtgacgaac agctgaagtc cggacagct agcgtggtct gtctgctgaa caattttac        480 cccagggaag ccaaagtgca gtggaaggtc gataacgctc tgcagtctgg aaatagtcag      540
gagtcagtga cagaacagga ctccaaagat agcacttatt ctctgtctag taccctgaca      600
ctgagcaagg cagactacga aagcataaa gtgtatgcct gtgaagtcac tcatcagggg       660
```

```
ctgtccagtc ccgtcacaaa atcctttaat cgtggcgaat gttga            705
```

<210> SEQ ID NO 40
<211> LENGTH: 234
<212> TYPE: PRT
<213> ORGANISM: Artificial Sequence
<220> FEATURE:
<223> OTHER INFORMATION: synthetic

<400> SEQUENCE: 40

```
Met Arg Val Pro Ala Gln Leu Leu Gly Leu Leu Leu Trp Leu Arg
1               5                   10                  15

Gly Ala Arg Cys Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

BISPECIFIC COUPLED ANTIBODY, PREPARATION METHOD AND APPLICATION THEREOF

CROSS-REFERENCE TO RELATED APPLICATIONS

This application is a continuation-in-part of International Patent Application No. PCT/CN2016/110438 with a filing date of Dec. 16, 2016, designating the United States, now pending, and further claims priority to Chinese Patent Application No. 201510953199.3 with a filing date of Dec. 16, 2015. The content of the aforementioned applications, including any intervening amendments thereto, are incorporated herein by reference.

TECHNICAL FIELD

The present disclosure belongs to the field of biological medicine, and particularly belongs to the field of anti-tumor immunotherapy of double-target monoclonal antibodies.

BACKGROUND OF THE PRESENT INVENTION

Her-2 is an epidermal growth factor receptor transmembrane protein coded by oncogenes HER-2, and an intracellular domain of receptor proteins has tyrosine kinase activity. When the Her-2 forms a homodimer or forms a heterodimer with other receptor members in families thereof, tyrosine kinases in the intracellular domain are activated, and multiple intracellular signal paths are activated. The major signal path has the functions of stimulating cell growth and division as well as resisting apoptosis and maintaining cell survival. It is discovered that lots of HER-2 genes are replicated or mutated in cancer cells of nearly ⅓ of breast cancer patients, so that HER-2 proteins are overexpressed or continuously activated, causing cell carcinogenesis. A trastuzumab monoclonal antibody with Her-2 inhibitory activity taking the Her-2 as a target is developed, and is the first humanized monoclonal antibody approved to be used for treating Her-2 positive breast cancer patients. A single trastuzumab monoclonal antibody drug has curative effects on treatment of 11-26% of patients with malignant breast cancer, and if the single trastuzumab monoclonal antibody drug is used together with chemotherapy, cure rates and survival rates of patients with early breast cancer and advanced breast cancer will be obviously increased. Although such good curative effects are achieved, quite a portion of Her-2 positive patients still do not have any response to the trastuzumab, and with respect to patients with response at an early treatment stage, a majority of the patients will produce resistance to trastuzumab monoclonal antibody treatment during late treatment.

The activity of the trastuzumab monoclonal antibody for inhibiting tumors depends on the Her-2 inhibitory activity and trastuzumab monoclonal antibody induced antibody-dependent cell-mediated cytotoxicity (ADCC). It is proved that an anti-Her-2 antibody which cannot be bound with an IgGFc receptor (FcR) does not have an anti-tumor effect, and it is also proved that in mice with FcR gene deletion, the trastuzumab monoclonal antibody does not have any curative effect. In addition, it is discovered that, FcR positive immune cells (mainly natural killer cells) are increased in breast tumor biopsies of patients subjected to trastuzumab monoclonal antibody treatment. These data indicate that activity of an innate immune system ADCC is one of the trastuzumab monoclonal antibody tumor inhibition mechanisms. Besides this, acquired immunity also achieves an important effect in tumor inhibition effect of the trastuzumab monoclonal antibody. In a mouse Her-2 positive breast tumor model with immunological competence, in order to achieve a better antitumor effect, the anti-Her-2 antibody needs CD8α+ cells, MyoD88 signal paths and RAG-dependent acquired immunity activity. Further study proves that, the traditional lymphocyte-mediated interleukin toxicity type I interferon (INF-I) and interferon gamma (INFγ) are very important to the tumor inhibition effect of the trastuzumab monoclonal antibody, wherein INFγ produced by CD8α+ T cells plays a key role. Recombinant INFγ can directly inhibit in-vitro growth of Her-2 positive tumor cells and obviously enhance ability of the Her-2 antibody for inhibiting cell growth. In addition, the INFγ obviously increases expressions of type I MHC on tumor cell surfaces. By combining the data, the significance of the INFγ in the tumor inhibition effect of the trastuzumab monoclonal antibody is explained.

Since the acquired immunity activity has such an importance in the tumor inhibition effect of the trastuzumab monoclonal antibody, the tumor inhibition effect of the trastuzumab monoclonal antibody may be enhanced by enhancing activation of the immune cells or maintaining the activation of the immune cells. In fact, studies have found that, when the trastuzumab monoclonal antibody is used together with an anti-CD137 monoclonal antibody, survival of lymphocytes is enhanced, particularly survival ability of CD8+ T cells. The CD137 antibody can further enhance activation and functions of NK cells and DC cells, and the antitumor effect of the anti-Her-2 antibody is enhanced by virtue of FcR+ cells and acquired immunity cells. In addition, a PD-1 path is blocked by a programmed cell death-1 (PD-1) antibody, and the trastuzumab monoclonal antibody induced acquired immunity T cell antitumor activity can be obviously increased.

Activation of the T cells needs stimulation of an MHC-peptide complex on a T cell receptor on antigen presenting cells (APCs) and also needs balance between a co-stimulatory signal and an inhibitory signal. Multiple mechanisms interact to mediate activation of CD4+ and CD8+T lymphocytes together, including amplification or inhibition of cell surface proteins with T cell response. Negative regulatory proteins on surfaces of the T cells, such as CTLA-4, PD-1, B7 family molecules B7-H4, T cell immune molecules and lymphocyte activating gene-3 (LAG-3) and ligand combinations thereof on different types of cells may cause decrease of T cell growth and functional activity. In order to effectively control the activated immune cells and produce effective immune response, it is necessary for the organism to strictly regulate expressions of the negative regulatory proteins at immune checkpoints. Exposure of common chronic antigens in cancers and some virus infections may enable antigen-specific T lymphocytes to continuously express the molecules such as the CTLA-4, PD-1 and LAG-3, thereby causing antigen tolerance by adjacent cells. Therefore, development of drugs that take the negative regulatory proteins at immune checkpoints as targets receives a great attention.

A CD28 molecule is a protein that is continuously expressed and belongs to immunoglobulin family, and can mediate T cell co-stimulatory signals. The CD28 is bound to ligands B7-1 and B7-2 on the APC so as to induce the production of interleukin-2 (IL-2) and antiapoptosis factors, thereby stimulating growth of the T cells. After the T cells are activated, the CTLA-4 is produced on the cell surface, is very similar to the CD28 molecule, can be bound with the B7-1 and B7-2, and has higher binding strength and affinity (particularly bound to the B7-1). Therefore, a trace amount of CTLA-4 molecule can be effectively and competitively bound with a ligand of the CD28, thereby decreasing the T cell response. In addition, the CTLA-4 has internal and external action mechanisms, including effects of eliminating regionalization of PKC-beta and CARMA1 from immune synapse, limiting existence time of the T cells and enhancing T regulatory cells (Tregs). In general, these mechanisms have effects of inhibiting the cell growth process, inhibiting production of the IL-2 and cell survival pathways and finally causing immune response end. CTLA-4 knockout mouse experiments well prove the significance of the CTLA-4 as a negative regulatory molecule. CTLA-4 immunodeficiency mice show CD28-dependent large-scale autoreactive T cell expansion in lymphonodi, spleens and several peripheral organs. Due to spreading diseases caused by lymphocyte growth, these mice die within less than four weeks after birth. The CTLA-4 as a main immune checkpoint molecule of the T cell reaction may influence memory formation of the acquired immunity response. Recent studies discover that, quantities of professional and multifunctional CD4+T memory cells may be decreased by blocking the CTLA-4, and quality of an overall memory cell pool is further regulated. Another in-vivo study discovers that, by virtue of injection of the CTLA-4 antibody, expanded CD8+T memory cells may be increased, and immune cells capable of producing INFg and INFa are accumulated.

Studies on different CTLA-4 monoclonal antibodies have proved that, selective blocking of the CTLA-4 can enhance internal or induced anti-tumor immune response, which provides a support for clinical development of a monoclonal antibody taking the CTLA-4 as a target. Two human complete antibodies, that is, Ipilimumab and Tremelimumab, can be bound with the CTLA-4 and block binding with the B7 ligand, thereby further enhancing activation and proliferation of the T cells. In the last 10 years, the Ipilimumab and Tremelimumab are subjected to lots of clinical studies related to melanoma treatment, and in 2011, the ipilimumab is approved to be used for treating unresectable or non-transferable melanoma by State Food and Drug Administration in America, European Union and Australia. Blocking of the CTLA-4 provides a novel immune system regulation mode, which indicates a milestone discovery in the field of tumor treatment. At present, the CTLA-4 monoclonal antibody treatment is performed in clinical tests of multiple types of tumors, including melanoma, small cell lung cancer, non-small cell lung cancer and prostatic cancer.

SUMMARY OF PRESENT INVENTION

A purpose of the present disclosure is to provide a bispecific coupled antibody as well as a preparation method and an application thereof.

In a first aspect, the present disclosure provides a heavy chain variable region of an antibody, and the heavy chain variable region comprises three complementary determining regions CDR as follows: CDR1 shown in SEQ ID NO:5, CDR2 shown in SEQ ID NO:6, and CDR3 shown in SEQ ID NO:7.

In another preferred embodiment, the heavy chain variable region has an amino acid sequence shown in SEQ ID NO:4.

In a second aspect, the present disclosure provides a heavy chain of an antibody, and the heavy chain has the heavy chain variable region in the first aspect of the present disclosure and a heavy chain constant region.

In another preferred embodiment, the heavy chain constant region is a humanized or murine region.

In a third aspect, the present disclosure provides a light chain variable region of an antibody, and the light chain variable region comprises complementary determining regions CDR selected from the following groups: CDR1' shown in SEQ ID NO:11, CDR2' shown in SEQ ID NO:12, and CDR3' shown in SEQ ID NO:13.

In another preferred embodiment, the light chain variable region has an amino acid sequence shown in SEQ ID NO:10.

In a fourth aspect, the present disclosure provides a light chain of an antibody, and the light chain has the light chain variable region in the third aspect of the present disclosure and a light chain constant region.

In another preferred embodiment, the light chain constant region is a humanized or murine region.

In a fifth aspect, the present disclosure provides an antibody, and the antibody comprises: (1) the heavy chain variable region according to the first aspect of the present disclosure; and/or (2) the light chain variable region according to the third aspect of the present disclosure.

In another preferred embodiment, the antibody has the heavy chain according to the second aspect of the present disclosure; and/or the light chain according to the third aspect of the present disclosure.

In another preferred embodiment, the antibody is a specific anti-CTLA-4 protein antibody.

In another preferred embodiment, the antibody comprises a single-chain antibody, a double-chain antibody, a monoclonal antibody, a chimeric antibody (such as a human-mouse chimeric antibody), a murine antibody, a humanized antibody, a bispecific antibody (BiTE) and a chimeric antigen receptor antibody (CAR).

In a sixth aspect, the present disclosure provides a recombinant protein, and the recombinant protein comprises: (i) the heavy chain variable region according to the first aspect of the present disclosure, the heavy chain according to the second aspect of the present disclosure, the light chain variable region according to the third aspect of the present disclosure, a sequence of the light chain in the fourth aspect of the present disclosure, or the antibody according to the fifth aspect of the present disclosure; and (ii) an optional tag sequence for assisting expression and/or purification.

In another preferred embodiment, the tag sequence comprises 6His tags.

In another preferred embodiment, the recombinant protein is specifically bound with a CTLA-4 protein.

In a seventh aspect, the present disclosure provides a multispecific antigen binding molecule, and the multispecific antigen binding molecule comprises: a first antigen binding domain (D1); and a second antigen binding domain (D2); the D1 is specifically bound with a target molecule Her-2 protein; and the D2 is specifically bound with a target molecule CTLA-4 protein.

In another preferred embodiment, inhibiting ability of the multispecific antigen binding molecule to Her-2 protein-positive tumors is higher than inhibiting ability of a monospecific antigen binding molecule of the Her-2 protein to the Her-2 protein-positive tumors.

In another preferred embodiment, the multispecific antigen binding molecule is a peptide.

In another preferred embodiment, the multispecific antigen binding molecule is an antibody.

In another preferred embodiment, the multispecific antigen binding molecule is a bispecific antibody.

In another preferred embodiment, the D1 is an antibody or an antibody fragment specifically bound with the Her-2 protein.

In another preferred embodiment, the D2 is an antibody or an antibody fragment specifically bound with the CTLA-4 protein.

In another preferred embodiment, the D1 and/or the D2 are (is) single-chain antibody fragments (scFv).

In another preferred embodiment, in the multispecific antigen binding molecule, only the D2 is the single-chain antibody fragment (scFv).

In another preferred embodiment, the D1 and the D2 are connected by a connecting peptide, and the connecting peptide comprises an antibody constant region sequence.

In another preferred embodiment, the D1 is an anti-Her-2 humanized antibody.

In another preferred embodiment, the D2 is an anti-CTLA-4 single-chain antibody fragment (scFv).

In another preferred embodiment, the D1 is the anti-Her-2 humanized antibody, the D2 is an anti-CTLA-4 single-chain antibody fragment (scFv), and the D2 is connected to the end of a heavy chain constant region of the D1.

In another preferred embodiment, the anti-Her-2 humanized antibody comprises complementary determining regions CDR in at least one heavy chain variable region selected from the following group: CDRa shown in SEQ ID NO:18, CDRb shown in SEQ ID NO:19, and CDRc shown in SEQ ID NO:20.

In another preferred embodiment, the anti-Her-2 humanized antibody comprises a heavy chain shown in SEQ ID NO:15.

In another preferred embodiment, the anti-Her-2 humanized antibody comprises complementary determining regions CDR' in at least one light chain variable region selected from the following group: CDRa' shown in SEQ ID NO:21, CDRb' shown in SEQ ID NO:22, and CDRc' shown in SEQ ID NO:23.

In another preferred embodiment, the anti-Her-2 humanized antibody comprises a light chain shown in SEQ ID NO:17.

In another preferred embodiment, the anti-CTLA-4 single-chain antibody fragment (scFv) comprises complementary determining regions CDR in at least one heavy chain variable region selected from the following group: CDR1 shown in SEQ ID NO:5, CDR2 shown in SEQ ID NO:6, and CDR3 shown in SEQ ID NO:7.

In another preferred embodiment, the anti-CTLA-4 single-chain antibody fragment (scFv) comprises a heavy chain variable region shown in SEQ ID NO:4.

In another preferred embodiment, the anti-CTLA-4 single-chain antibody fragment (scFv) comprises complementary determining regions CDR' in at least one light chain variable region selected from the following group: CDR1' shown in SEQ ID NO:11, CDR2' shown in SEQ ID NO:12, and CDR3' shown in SEQ ID NO:13.

In another preferred embodiment, the anti-CTLA-4 single-chain antibody fragment (scFv) comprises a light chain variable region shown in SEQ ID NO:10.

In another preferred embodiment, a sequence of the anti-CTLA-4 single-chain antibody fragment (scFv) is shown in SEQ ID NO:24.

In an eighth aspect, the present disclosure provides a polynucleotide for coding peptides selected from the following group: (1) the heavy chain variable region in the first aspect of the present disclosure, the heavy chain in the second aspect of the present disclosure, the light chain variable region in the third aspect of the present disclosure, the light chain in the fourth aspect of the present disclosure, or the antibody in the fifth aspect of the present disclosure; or (2) the recombinant protein in the sixth aspect of the present disclosure, or the multispecific antigen binding molecule in the seventh aspect of the present disclosure.

In a ninth aspect, the present disclosure provides a carrier, and the carrier comprises the polynucleotide according to the eighth aspect of the present disclosure.

In another preferred embodiment, the carrier comprises bacterial plasmids, phages, yeast plasmids, plant cell viruses, mammalian cell viruses such as adenoviruses or retroviruses, or other carriers.

In a tenth aspect, the present disclosure provides a genetically engineered host cell comprising the carrier in the ninth aspect of the present disclosure or integrating the polynucleotide in the eighth aspect of the present disclosure in the genome.

In an eleventh aspect, the present disclosure provides an immunoconjugate, and the immunoconjugate comprises: (a) the heavy chain variable region in the first aspect of the present disclosure, the heavy chain in the second aspect of the present disclosure, the light chain variable region in the third aspect of the present disclosure, the light chain in the fourth aspect of the present disclosure, the antibody in the fifth aspect of the present disclosure, the recombinant protein in the sixth aspect of the present disclosure, or the multispecific antigen binding molecule in the seventh aspect of the present disclosure; and a coupled part selecting from the following group: detectable markers, drugs, toxins, cytokines, radionuclides or enzymes.

In another preferred embodiment, the coupled part is selected from: fluorescent or luminescent markers, radioactive markers, MRI (Magnetic Resonance Imaging) or CT (Computed Tomography) contrast agents, or enzymes capable of producing detectable products, radionuclides, biotoxins, cytokines (such as IL-2 and the like), antibodies, antibody Fc fragments, antibody scFv fragments, gold nanoparticles/nanorods, virus particles, lipidosome, magnetic nanoparticles, prodrug activating enzymes (such as, DT-diaphorase (DTD) or biphenyl hydrolase-like protein (BPHL)), chemotherapeutic agents (such as cis-platinum) or nanoparticles of any form, and the like.

In a twelfth aspect, the present disclosure provides a pharmaceutical composition comprising: (i) the heavy chain variable region in the first aspect of the present disclosure, the heavy chain in the second aspect of the present disclosure, the light chain variable region in the third aspect of the present disclosure, the light chain in the fourth aspect of the present disclosure, the antibody in the fifth aspect of the present disclosure, the recombinant protein in the sixth aspect of the present disclosure, the multispecific antigen binding molecule in the seventh aspect of the present disclosure, or the immunoconjugate in the eleventh aspect of the present disclosure; and (ii) pharmaceutically acceptable carriers.

In another preferred embodiment, the pharmaceutical composition is of an injection dosage form.

In another preferred embodiment, the pharmaceutical composition is used for preparing drugs for treating tumors, wherein the tumors are selected from the following group: stomach cancer, liver cancer, leukemia, renal tumor, lung cancer, carcinoma of small intestine, osteocarcinoma, prostatic cancer, colorectal cancer, breast cancer, colorectal cancer, prostatic cancer, cervical cancer, adrenal tumor, or bladder tumor.

In a thirteenth aspect, the present disclosure provides applications of the heavy chain variable region in the first aspect of the present disclosure, the heavy chain in the second aspect of the present disclosure, the light chain variable region in the third aspect of the present disclosure, the light chain in the fourth aspect of the present disclosure, the antibody in the fifth aspect of the present disclosure, the recombinant protein in the sixth aspect of the present disclosure, the multispecific antigen binding molecule in the seventh aspect of the present disclosure or the immunoconjugate in the eleventh aspect of the present disclosure, used for preparing drugs, reagents, detection plates or kits.

The reagents, the detection plates or the kits are used for detecting CTLA-4 proteins in samples.

The drugs are used for treating or preventing tumors expressing CTLA-4 proteins.

In another preferred embodiment, the tumors comprise stomach cancer, lymphoma, liver cancer, leukemia, renal tumor, lung cancer, carcinoma of small intestine, osteocarcinoma, prostatic cancer, colorectal cancer, breast cancer, colorectal cancer, prostatic cancer or adrenal tumor.

In another preferred embodiment, the tumors are selected from stomach cancer and follicular lymphoma.

In another preferred embodiment, the reagents comprise chips and antibody-coated immune particles.

In a fourteenth aspect, the present disclosure provides a method for detecting a CTLA-4 protein in a sample, and the method comprises the following steps: (1) contacting the sample with the antibody in the fifth aspect of the present disclosure; and (2) detecting whether an antigen-antibody complex is formed, wherein the CTLA-4 protein exists in the sample if the complex is formed.

In a fifteenth aspect, the present disclosure provides a method for preparing a recombinant polypeptide, and the method comprises the steps: (a) culturing the host cell in the tenth aspect of the present disclosure under conditions suitable for expression; and (b) separating the recombinant polypeptide from the culture, wherein the recombinant polypeptide is the antibody in the fifth aspect of the present disclosure, or the recombinant protein in the sixth aspect of the present disclosure, or the multispecific antigen binding molecule in the seventh aspect of the present disclosure.

It should be understood that, in a scope of the present disclosure, above various technical features of the present disclosure and various technical features described specifically thereinafter (such as embodiments) may be combined with one another, so as to form new or preferred technical solutions. Due to the limit of the paper, the technical solutions are not described one by one herein.

DESCRIPTION OF THE DRAWINGS

FIG. 2 shows a nucleotide sequence and an amino acid sequence of a bispecific coupled antibody; FIG. 2(A) shows a nucleotide sequence (SEQ ID. NO: 37) and an amino acid sequence (SEQ ID. NO: 38) of a heavy chain, and FIG. 2(B) shows a nucleotide sequence (SEQ ID. NO: 39) and an amino acid sequence (SEQ ID. NO: 40) of a light chain; in FIG. 2(A), aa1-19 represents a protein transmembrane signal peptide, aa20-468 represents a heavy chain of a humanized anti-Her-2 monoclonal antibody (trastuzumab monoclonal antibody), aa469-586 represents a heavy chain variable region of a human antibody CTLA-4scFv, aa587-593 represents a connecting peptide of heavy chain and light chain variable regions of the human antibody CTLA-4scFv, and aa594-702 represents a light chain variable region of the human antibody CTLA-4scFv; in FIG. 2(B), aa1-20 represents a protein transmembrane signal peptide, and aa21-234 represents a light chain of the humanized anti-Her-2 monoclonal antibody (trastuzumab monoclonal antibody);

DETAILED DESCRIPTION OF PREFERRED EMBODIMENTS

Figure 1:
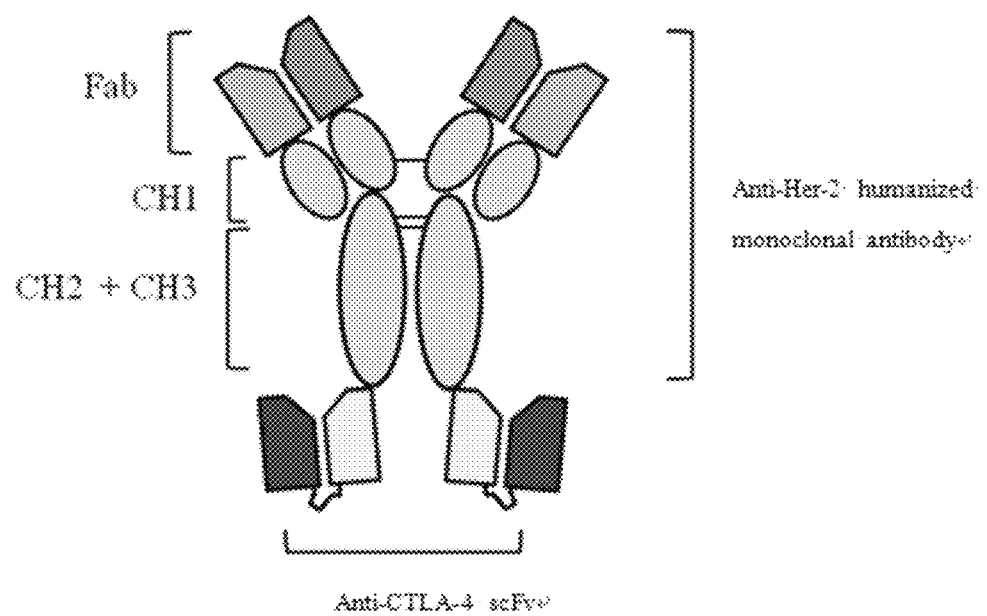
FIG. 1 shows a structural schematic diagram of a bispecific coupled antibody, an upper part of the structural diagram is heavy chain and light chain variable regions of a trastuzumab monoclonal antibody represented by different colors, a lower part of the structural diagram is scFv of a humanized anti-CTLA-4 monoclonal antibody, a heavy chain variable region of the scFv antibody is connected with a C terminal of the heavy chain of the trastuzumab monoclonal antibody, and a connecting peptide with 7 amino acids exists between the heavy chain variable region and the light chain variable region of the scFv.

The inventor obtains an anti-CTLA-4 humanized single-chain antibody fragments (scFv) by virtue of extensive and in-depth studies. The anti-CTLA-4 antibody has the advantages of high affinity and strong specificity. On this basis, the inventor accidentally discovers that, by constructing a recombinant bispecific coupled antibody (fused by a humanized anti-Her-2 complete antibody (trastuzumab) and the anti-CTLA-4 humanized single-chain antibody fragment (scFv)) by using the anti-CTLA-4 antibody, immune response of an organism may be obviously enhanced, an activated state of T cells may be maintained or enhanced, curative effects of treating Her-2 positive breast cancer by trastuzumab may be enhanced, and the Her-2 positive breast cancer resistant to the trastuzumab is treated. A bispecific coupled antibody in the present disclosure is not limited to treatment of the Her-2 positive breast cancer and can also treat Her-2 positive malignant tumors of other types.

Before the present invention is specifically described, it should be understood that, the present invention is not limited to specific methods and experimental conditions since these methods and conditions are variable. It should be further understood that, a purpose of terms used in the text is to describe specific embodiments only, not intended to be restrictive. A scope of the present disclosure is limited by claims only.

Unless additionally defined, all technical and scientific terms used in the present disclosure have the same meanings as generally understood by those ordinary skilled in the art to which the present disclosure belongs. For example, when used in a specifically listed numerical value in the present disclosure, a term "about" indicates that the value may be varied from the listed value by not more than 1%, e.g., as used in the present disclosure, a term "about 100" includes all values between 99 and 101 (such as 99.1, 99.2, 99.3, 99.4 and the like).

Although any method and material similar or equivalent to description in the present disclosure may be used in embodiments or tests of the present disclosure, preferred methods and materials are listed herein.

CTLA-4 Protein

The present disclosure provides a multispecific antigen binding molecule comprising a first antigen binding domain (D1) and a second antigen binding domain (D2), wherein the second antigen binding domain D2 is specifically bound with a CTLA-4 protein.

In a preferred embodiment, an amino acid sequence of extracellular fragments of the CTLA-4 protein is as follows:

```
                                        (SEQ ID NO.: 1)
AMHVAQPAVVLASSRGIASFVCEYASPGKATEVRVTVLRQADSQVTEVCA
ATYMMGNELTFLDDSICTGTSSGNQVNLTIQGLRAMDTGLYICKVELMYP
PPYYLGIGNGTQIYVIDPEPCPDSDF
```

Her-2 Protein

In context of the present disclosure, the D1 component of the multispecific antigen binding molecule is specifically bound with an extracellular ligand binding region of a target molecule Her-2 protein.

The Her-2 protein belongs to an epidermal growth factor receptor family (EGFR), and is composed of the extracellular ligand binding region, a single-chain transmembrane region and an intracellular protein tyrosine kinase region. The ligand binding region is bound with a ligand of the Her-2 protein, so as to transfer extracellular signals into cells, activate an EGFR signal path and promote cell carcinogenesis.

In a preferred embodiment, an amino acid sequence of extracellular fragments of the Her-2 protein is as follows:

```
                                        (SEQ ID NO.: 2)
TQVCTGTDMKLRLPASPETHLDMLRHLYQGCQVVQGNLELTYLPTNASLS
FLQDIQEVQGYVLIAHNQVRQVPLQRLRIVRGTQLFEDNYALAVLDNGDP
LNNTTPVTGASPGGLRELQLRSLTEILKGGVLIQRNPQLCYQDTILWKDI
FHKNNQLALTLIDTNRSRACHFCSPMCKGSRCWGESSEDCQSLTRTVCAG
GCARCKGPLPTDCCHEQCAAGCTGPKHSDCLACLHFNHSGICELHCPALV
TYNTDTFESMPNPEGRYTFGASCVTACPYNYLSTDVGSCTLVCPLHNQEV
TAEDGTQRCEKCSKPCARVCYGLGMEHLREVRAVTSANIQEFAGCKKIFG
SLAFLPESFDGDPASNTAPLQPEQLQVFETLEEITGYLYISAWPDSLPDL
SVFQNLQVIRGRILHNGAYSLTLQGLGISWLGLRSLRELGSGLALIHHNT
HLCFVHTVPWDQLFRNPHQALLHTANRPEDECVGEGLACHQLCARGHCWG
PGPTQCVNCSQFLRGQECVEECRVLQGLPREYVNARHCLPCHPECQPQNG
SVTCFGPEADQCVACAHYKDPPFCVARCPSGVKPDLSYMPIWKFPDEECT
ACQPCPINCTHSCVDEDDKGCPAEQRASPLT.
```

Anti-CTLA-4 Protein

The present disclosure provides an anti-CTLA-4 antibody. A heavy chain variable region of the antibody comprises three complementary determining regions CDR as follows: CDR1: SYGMH (SEQ ID NO:5); CDR2: VIWYDGSRQYYADS (SEQ ID NO:6); CDR3: GGFW-GAFDI (SEQ ID NO:7).

In another preferred embodiment, the heavy chain variable region has an amino acid sequence shown in SEQ ID NO:4:

```
                                        (SEQ ID NO.: 4)
QVQLVQSGGGVVQPGRSLRLSCAASGFTFSSYGMHWVRQAPGKGLEWVAV
IWYDGSRQYYADSVKGRFTISRDDSKNTMYLQMNSLRAEDTAVYYCARGG
FWGAFDIWGQGTMVTVSS.
```

A coded nucleotide sequence is as follows:

```
                                        (SEQ ID NO.: 3)
CAGGTCCAGCTGGTGCAGTCTGGGGGAGGCGTGGTCCAGCCTGGGAGGTC
CCTGAGACTCTCCTGTGCAGCGTCTGGATTCACCTTCAGTAGCTATGGCA
TGCACTGGGTCCGCCAGGCTCCAGGCAAGGGGCTGGAGTGGGTGGCAGTT
ATATGGTATGATGGAAGTAGGCAATATTATGCTGACTCCGTGAAGGGCCG
ATTCACCATCTCCAGAGACGATTCCAAGAACACGATGTATCTGCAAATGA
ACAGCCTGAGAGCCGAAGACACGGCTGTTTAFTACTGTGCGAGAGGGGGA
TTTTGGGGGGCTTTTGATATCTGGGGCCAAGGGACAATGGTCACCGTCTC
CTCA.
```

In another preferred embodiment of the present disclosure, a light chain variable region of the CTLA-4 antibody comprises complementary determining regions CDR selecting from the following groups: CDR1': RASQHVISSYLA (SEQ ID NO:11); CDR2': GASSRDT (SEQ ID NO:12); and CDR3': QQYGTSPWTF (SEQ ID NO:13).

In another preferred embodiment, a light chain variable region of the CTLA-4 antibody has an amino acid sequence shown in SEQ ID NO:10:

(SEQ ID NO.: 10)
DVVMTQSPGTLSLSPGEGATLSCRASQHVISSYLAWYQQKPGQAPRLLVY
AGSSRDTGVSDRFTGSGSGTDFTLTISRLEPEDSAVYFCQQYGTSPWTFG
QGTKLEIKR.

A coded nucleotide sequence is as follows:

(SEQ ID NO.: 9)
GATGTTGTGATGACTCAGTCTCCAGGCACCCTGTCTTTGTCTCCAGGGGA

AGGAGCCACACTCTCCTGCAGGGCCAGTCAACATGTTATCAGCAGCTACT

TAGCCTGGTATCAGCACCTGGCCAGGCTCCCAGGCTCCTCGTCTACGGTG

CATCCAGTAGGGACACTGGCGTCTCAGACAGGTTCACTGGCAGTGGGTCT

GGGACAGACTTCACTCTCACCATCAGCAGACTGGAGCCTGAAGATTCTGC

GGTGTATTTCTGTCAGCAGTATGGTACATCACCGTGGACGTTCGGCCAAG

GGACCAAGCTGGAGATCAAACGT.

In another preferred embodiment of the present disclosure, the CTLA-4 antibody is a single-chain antibody. Optionally, a connecting peptide exists between a heavy chain variable region and a light chain variable region of the CTLA-4 antibody. Preferably, a length of the connecting peptide is 1-15 amino acids, preferably 3-10 amino acids. Preferably, an amino acid sequence of the connecting peptide is as follows:

(SEQ ID NO.: 8)
GSGGGGS.

Multispecific Antigen Binding Molecule

The inventor is surprised to discover that, a multispecific antigen binding molecule comprising a specific binding target molecule Her-2 protein binding domain and a specific binding target molecule CTLA-4 protein binding domain constructed in the present disclosure has obvious inhibitory effects on Her-2 positive tumors, can achieve effects of enhancing curative effects of the trastuzumab on the Her-2 positive tumors and treating the Her-2 positive tumors resistant to the Trastuzumab, and can serve as a sensitizer of the trastuzumab.

Therefore, the present disclosure provides a multispecific antigen binding molecule comprising a first antigen binding domain (also called "D1" hereinafter) and a second antigen binding domain (also called "D2" hereinafter), wherein the D1 is specifically bound with the target molecule Her-2 protein; and the D2 is specifically bound with the target molecule CTLA-4 protein.

According to the present disclosure, the multispecific antigen binding molecule may be a single multifunctional peptide, or may be a polymer complex formed by performing covalent or noncovalent binding on two or more peptides with one another. For example, since the present disclosure becomes apparent, any antigen binding structure with ability of simultaneously binding the Her-2 and CTLA-4 molecules is considered as the multispecific antigen binding molecule.

Any multispecific antigen binding molecule or variants thereof in the present disclosure may be constructed by using a standard molecular biology technology (such as, a recombinant DNA and protein expression technology), which will be known by those ordinary skilled in the art.

In a preferred embodiment of the present disclosure, the specific binding target molecule Her-2 protein binding domain comprises complementary determining regions CDR in at least one heavy chain variable region selected from the following groups: CDRa: GFNIKDTY (SEQ ID NO:18), CDRb: IYPTNGYT (SEQ ID NO:19), and CDRc: SRWGGDGFYAMDY (SEQ ID NO:20).

In another preferred embodiment, the specific binding target molecule Her-2 protein binding domain comprises a heavy chain shown in SEQ ID NO. :15 as follows:

(SEQ ID NO.: 15)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPG.

A coded nucleotide sequence is shown in SEQ ID NO. :14.

In another preferred embodiment, the specific binding target molecule Her-2 protein binding domain comprises complementary determining regions CDR' in at least one light chain variable region selected from the following groups: CDRa': QDVNTA (SEQ ID NO:21), CDRb': SASFLYS (SEQ ID NO:22), and CDRc': QQHYTTPPT (SEQ ID NO:23).

In another preferred embodiment, the specific binding target molecule Her-2 protein binding domain comprises a light chain shown in SEQ ID NO. :17 as follows:

(SEQ ID NO.: 17)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

A coded nucleotide sequence is shown in SEQ ID NO. :16.

In another preferred embodiment of the present disclosure, the specific binding target molecule CTLA-4 protein binding domain comprises complementary determining regions CDR in at least one heavy chain variable region selected from the following groups: CDR1 shown in SEQ ID NO:5, CDR2 shown in SEQ ID NO:6, and CDR3 shown in SEQ ID NO:7.

In another preferred embodiment, the specific binding target molecule CTLA-4 protein binding domain comprises a heavy chain variable region shown in SEQ ID NO. :4.

In another preferred embodiment, the specific binding target molecule CTLA-4 protein binding domain comprises complementary determining regions CDR' in at least one light chain variable region selected from the following groups: CDR1' shown in SEQ ID NO:11, CDR2' shown in SEQ ID NO:12, and CDR3' shown in SEQ ID NO:13.

In another preferred embodiment, the specific binding target molecule CTLA-4 protein binding domain comprises a light chain variable region shown in SEQ ID NO. :10.

In another preferred embodiment, the specific binding target molecule CTLA-4 protein binding domain is an anti-CTLA-4 single-chain antibody fragment (scFv) having a sequence shown in SEQ ID NO. :24:

(SEQ ID NO.: 24)
QVQLVQSGGGVVQPGRSLRLSCAASGFTFSSYGMHWVRQAPGKGLEWVAV

IWYDGSRQYYADSVKGRFTISRDDSKNTMYLQMNSLRAEDTAVYYCARGG

FWGAFDIWGQGTMVTVSSGSGGGGSDVVMTQSPGTLSLSPGEGATLSCRA

SQHVISSYLAWYQQKPGQAPRLLVYGASSRDTGVSDRFTGSGSGTDFTLT

ISRLEPEDSAVYFCQQYGTSPWTFGQGTKLEIKR.

In another preferred embodiment of the present disclosure, in the multispecific antigen binding molecule, the anti-CTLA-4 single-chain antibody fragment is connected to a C terminal of a heavy chain of the trastuzumab.

Antigen Binding Domain

The multispecific antigen binding molecule in the present disclosure comprises at least two independent antigen binding domains (D1 and D2). As mentioned in the present disclosure, the expressed "antigen binding domain" means any of peptides, polypeptides, nucleic acid molecules, stent molecules, peptide display molexcules or polypeptide-containing constructs that can be specifically bound with a specific target antigen.

As used in the present disclosure, a term "specific binding" means a process of forming a complex between the antigen binding domain and a specific antigen that takes a dissociation constant (KD) of 500 pM or less, and other irrelevant antigens are not bound under general test conditions. Preferably, the "irrelevant antigens" are proteins, peptides or polypeptides with amino acid identity less than 95% with one another.

Exemplary classifications of the antigen binding domains used in the context of the present disclosure comprise antibodies, antigen binding parts of the antibodies, peptides (such as peptibody) in specific interactions with specific antigens, acceptor molecules in specific interactions with the specific antigens, proteins comprising ligand binding parts specifically bound with receptors of the specific antigens, antigen binding stents (such as DARPin, HEAT repeat proteins, ARM repeat proteins, triangular tetrapeptide repeat proteins and other stents based on natural existence repeat proteins [see, e.g., Boersma and Pluckthun, 2011, *Curr. Opin. Biotechnol.* 22:849-857, and other references cited]) and aptamers or parts thereof.

Methods for determining whether two molecules are in specific binding are well-known in the art and comprise an equilibrium dialysis method, a surface plasma resonance method and the like. For example, as used in the context of the present disclosure, the antigen binding domains comprise polypeptides that are measured in the surface plasma resonance determination method and bound with specific antigens or parts thereof at $K_D$ of less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM or less than about 0.05 pM.

As used in the present disclosure, a term "surface plasma resonance" refers to an allowed BIAcore™ system (Department BiacoreLifeSciences in GEHealthcare, Piscataway, N.J.). A real-time interactive optical phenomenon is analyzed by detecting changes of protein concentrations inside a biosensor matrix).

As used in the present disclosure, a term "$K_D$" means an equilibrium dissociation constant of specific protein-protein interactions (e.g., antibody-antigen interactions). Unless additionally defined, the $K_D$ value in the disclosure is a $K_D$ value determined at 25° C. by the surface plasma resonance determination method.

Binding Fragment of Antibody and Antigen of Antibody

As mentioned above, the "antigen binding domain" (D1 and/or D2) may include an antibody or antigen binding fragments of the antibody or is composed of the antibody or the antigen binding fragments of the antibody. As used in the present disclosure, a term "antibody" means any antigen binding molecule or molecular complex comprising at least one complementary determining region (CDR) that is specifically bound with a specific antigen (such as, a Her-2 protein or a CTLA-4 protein) or interacts with the specific antigen. The term "antibody" comprises an immunoglobulin molecule comprising 4 polypeptide chains (two heavy chains (H) and two light chains (L) connected with one another by disulfide bonds) and polymers thereof (such as IgM). Each of the heavy chains includes a heavy chain variable region (HCVR or $V_H$ for short herein) and a heavy chain constant region. The heavy chain constant region includes 3 domains: $C_H1$, $C_H2$ and $C_H3$. Each of the light chains includes a light chain variable region (LCVR or $V_L$ for short herein) and a light chain constant region. The light chain constant region includes a domain ($C_L1$). The $V_H$ regions and the $V_L$ regions may be further divided into hypervariable regions named as complementary determining regions (CDR), and more conservative regions are inserted among the CDRs and named as framework regions (FR). Each of the $V_H$ and $V_L$ regions are composed of 3 CDRs and 4 FRs from an amino terminal to a carboxyl terminal according to a following sequence: FR1, CDR1, FR2, CDR2, FR3, CDR3 and FR4. In different embodiments of the present disclosure, the FRs of the antibody (or the antigen binding part thereof) in the present disclosure may be the same as a phylogenetic sequence or may be naturally or manually modified. A consensus sequence of amino acids may be defined based on parallel analysis of two or more CDRs.

The component D1 and/or D2 of the multispecific antigen binding molecule in the present disclosure may include or is composed of antigen binding fragments of a complete antibody molecule. As used in the present disclosure, terms "antigen binding part" of the antibody, "antigen binding fragments" of the antibody and the like include polypeptides or glycoproteins that are specifically bound with antigens in any natural existence form of the formed complex and are enzymatically available, synthetic or genetically modified. Any appropriate standard technology, such as a recombinant genetic engineering technology for performing enzymatic digestion of proteins or involved operations and expressing DNA with coded antibody variable domains and optional antibody constant domain, may be used, e.g., antigen binding fragments of the antibody are derived from the complete antibody molecule. The DNA is known and/or is easily available from a commercial source, a DNA library (including a phage antibody library) or may be synthesized. The DNA may be sequenced or operated chemically or by virtue of a molecular biological technique, e.g., an appropriate layout arranged by one or more variable domains and/or constant domains, or introduction of codons, production of cysteine residues, modification, addition or deletion of amino acids and the like.

Non-restrictive examples of the antigen binding fragments include: (i) Fab fragments; (II) F(ab')2 fragments; (iii) Fd fragments; (iv) Fv fragments; (v) single-chain Fv (scFv) molecules; (vi) dAb fragments; and (vii) minimal recognition units composed of amino acid residues in a simulative antibody hypervariable region (e.g., independent complementary determining regions (CDR) such as CDR3 peptides) or bound FR3-CDR3-FR4 peptides. As used in the present disclosure, other engineering molecules, such as domain-specific antibodies, monodomain antibodies, domain deletion antibodies, chimeric antibodies, CDR-grafted antibodies, diabodies, triple antibodies, tetra-antibodies, mini-antibodies, nano bodies (such as monovalent nano bodies, bivalent nano bodies and the like), small module immune preparations (SMIP) and shark variable IgNAR domains, are also included in the expressed "antigen binding fragments".

The antigen binding fragment of the antibody generally includes at least one variable domain. The variable domain may have any size or is composed of amino acids and generally includes at least one CDR that is adjacent to one or more frameworks or accords with a readable framework. In antigen binding fragments having $V_H$ domains associated with $V_L$ domains, the domains $V_H$ and $V_L$ domains may be set opposite to each other according to any appropriate arrangement. For example, the variable regions may be dimers and contain dimers $V_H$-VH, $V_H$-$V_L$ or $V_L$-$V_L$. Optionally, the antigen binding fragments of the antibody may include monomer $V_H$ or $V_L$ domains.

In some embodiments, the antigen binding fragments of the antibody may include at least one variable domain in covalent linkage with at least one constant domain. Non-restrictive and exemplary layouts of the variable domains and the constant domains inside the antigen binding fragments of the antibody in the present disclosure may include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii); $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. Any of the listed exemplary layouts above is included in any layout of the variable domains and the constant domains. The variable domains and the constant domains may be directly connected with each other or may be connected by virtue of complete or partial hinge regions or joint regions. Each of the hinge regions may be composed of at least 2 (such as, 5, 10, 15, 20, 40, 60 or more) amino acids that produce flexible connection or semi-flexible connection between adjacent variable domains and/or constant domains in a single polypeptide molecule. In addition, the antigen binding fragments may include homodimers or heterodimers (or other polymers) located in non-covalent association with each other having the layout with any of the listed variable domains and constant domains and/or with one or more monomer $V_H$ or $V_L$ domains.

The multispecific antigen binding molecule in the present disclosure may include a human antibody or a recombinant human antibody or fragments thereof or is composed of the human antibody or the recombinant human antibody or the fragments thereof. As used in the present disclosure, a term "human antibody" comprises an antibody with a variable region and a constant region derived from a human immunoglobulins sequence. However, the human antibody may comprise amino acid residues (such as, mutation introduced by virtue of in-vitro random mutagenesis or site-specific mutagenesis or in-vivo somatic mutation) that are not coded by the human immunoglobulins sequence (such as, in CDRs, particularly in CDR3), while as used in the present disclosure, the term "human antibody" is not intended to comprise an antibody in which a CDR sequence derived from a germ line of another mammalian species (such as mice) onto a human framework sequence.

The multispecific antigen binding molecule in the present disclosure may include or is composed of a recombinant human antibody or antigen binding fragments. As used in the present disclosure, a term "recombinant human antibody" is intended to comprise all human antibodies prepared, expressed, produced or separated by virtue of recombination means, e.g., antibodies expressed by recombinant expression vectors transfected into host cells (further described thereinafter), antibodies separated from recombinant human immunoglobulin combinatorial library (further described thereinafter), antibodies separated from transgenic animals (such as, mice) relative to human immunoglobulins genes (see, e.g., Taylor et al., (1992) Nucl. Acids Res. 20:6287-6295), or antibodies prepared, expressed, produced or separated by virtue of any other means involved for splicing human immunoglobulins gene sequences onto other DNA sequences. The recombinant human antibodies have variable regions and constant regions derived from the human immunoglobulins gene sequences. However, in some embodiments, the recombinant human antibodies are subjected to in-vitro mutagenesis (or, when used in the transgenic animals with respect to the human Ig sequence, subjected to in-vivo somatic cell mutagenesis), and although the amino acid sequences in the $V_H$ and $V_L$ regions of the recombinant antibodies are derived from the human $V_H$ and $V_L$ sequences and correlated to the human $V_H$ and $V_L$ sequences, natural sequences do not exist inside the human antibody library in vivo.

Bispecific Antibody

According to some embodiments, the multispecific antigen binding molecule in the present disclosure is a bispecific antibody, e.g., a bispecific antibody containing an antigen binding arm of a specific binding target molecule Her-2 and an antigen binding arm of a specific binding CTLA-4 protein. The multispecific antigen binding molecule in the present disclosure may be constructed by adopting a method for producing the bispecific antibody known in the art. Exemplary bispecific styles used in the context of the present disclosure may include, but not limited to a bispecific style based on scFv or a diabody, an IgG-scFv fusion, double variable domain (DVD)-Ig, cell hybridoma (Quadroma), binding-in buckle, a common light chain (such as, a common light chain with the binding-in buckle, and the like), CrossMab, CrossFab, (SEED) body, a leucine zipper, Duobody, IgG1/IgG2, dual-effect Fab(DAF)-IgG and a Mab² bispecific style (with respect to overview of the above styles, seed in Klein et al., 2012, mAbs 4:6,1-11, and references therein).

Polymer Component

According to some embodiments, the multispecific antigen binding molecule in the present disclosure may further comprise one or more polymer components. The polymer component may achieve an effect of maintaining association between the antigen binding domains (D1 and D2). As used in the present disclosure, the "polymer component" is any of macromolecules, proteins, polypeptides, peptides or amino acids having abilities of associating with a second polymer component with the same or similar structure or construct. For example, the polymer component may be a polypeptide including an immune globulin $C_H3$ domain. A non-restrictive example of the polymer component is an Fc part of the immune globulin, e.g., an Fc domain selected from isotype IgG1, IgG2, IgG3 and IgG4 and any of allotype IgG inside each of isotype groups. In some embodiments, the polymer component is an Fc fragment with a length of 1 to about 200 amino acids containing at least one cysteine residue, or an amino acid sequence. In other embodiments, the polymer component is the cysteine residue or an oligopeptide containing the cysteine. Other polymer structures comprise peptides or polypeptides containing leucine zippers, helix-loop motifs or coiled helix motifs or peptides or polypeptides composed of the leucine zippers, helix-loop motifs or coiled helix motifs.

In some embodiments, the multispecific antigen binding molecule in the present disclosure includes two polymer domains M1 and M2, wherein the D1 is connected with the M1 and the D2 is connected with the M2, and association between the M1 and the M2 promotes the D1 and D2 in a single multispecific antigen binding molecule to be physically connected with each other. In some embodiments, the M1 and the M2 are the same as each other. For example, the M1 may be an Fc domain with a specific amino acid sequence, and the M2 is an Fc domain with the same amino acid sequence as the M1. Optionally, the M1 and the M2 can be different from each other at one or more amino acid positions. For example, the M1 may include a first immune globulin (Ig)$C_H3$ domain and the M2 may include a second Ig$C_H3$ domain, wherein the first and second Ig$C_H3$ domains have the difference of at least one amino acid, and compared with a reference construct with the same M1 and M2 sequences, the difference of the at least one amino acid decreases binding between a target construct and a protein A. In one embodiment, the Ig$C_H3$ domain of the M1 is bound with the protein A, and the Ig$C_H3$ domain of the M2 contains mutation of decreasing or eliminating the binding effect of the protein A, such as H95R modification (according to an IMGT exon number, according to an EU number of H435R). The $C_H3$ of the M2 may further include Y96F modification (according to an IMGT number, according to an EU number of Y436F). Other modifications in the $C_H3$ of the M2 may include: D16E, L18M, N44S, K52N, V57M and V82I under conditions of an IgG1Fc domain (according to the IMGT number, according to EU numbers of D356E, L358M, N384S, K392N, V397M and V422I); N44S, K52N and V82I under conditions of an IgG2Fc domain (according to the IMGT number, according to EU numbers of N384S, K392N and V422I); and Q15R, N44S, K52N, V57M, R69K, E79Q and V82I under conditions of an IgG4Fc domain (according to the IMGT number, according to EU numbers of Q355R, N384S, K392N, V397M, R409K, E419Q and V422I).

Tumor Targeting

According to another aspect of the present disclosure, the multispecific antigen binding molecule can be used for targeting tumor cells.

The multispecific antigen binding molecule in the present disclosure can be conjugated with drugs, toxins, radioisotopes or other substances that damage cell survival. Optionally, the drugs or the toxins may be substances that do not directly kill cells but enable the cells to be easily killed by other external substances. In other additional embodiments involving the tumor targeting, the multispecific antigen binding molecule in the present disclosure is not conjugated with the drugs, the toxins or the radioisotopes, but are combined with other antigen binding molecules (called "accessory molecules" herein) to be applied, e.g., other antitumor antibodies.

According to some embodiments in the tumor targeting aspect of the present disclosure, the multispecific antigen binding molecule (or an accessory antibody) may be conjugated with one or more cytotoxic drugs selected from the followings: calicheamycin, esperamicin, methotrexate, doxorubicin, L-phenylalanine mustard, chlorambucil, ARA-C, vindesine, mitomycin C, cis-platinum, etoposide, bleomycin, 5-fluorouracil, estramustine, vincristine, etoposide, doxorubicin, taxol, larotaxel, testaxel, orataxel, docetaxel, dorastatin 10, auristatin E, auristatin PHE and maitansine-based compounds (such as, DM1, DM4 and the like). The multispecific antigen binding molecule (or the accessory antibody) may be or is optionally conjugated with the toxins, such as diphtherin, pseudomonasaeruginosa exotoxin A, ricin A chain, abrin A chain, volkensin A chain, α-sarcin, aleuritesfordii protein, dianthin, phytolacaamericana protein and the like. The multispecific antigen binding molecule (or the accessory antibody) may be or is optionally conjugated with one or more radioisotopes selected from the followings: $^{225}Ac$, $^{211}At$, $^{212}Bi$, $^{213}Bi$, $^{186}Rh$, $^{188}Rb$, $^{177}Lu$, $^{90}Y$, $^{131}I$, $^{67}Cu$, $^{125}I$, $^{123}I$, $^{77}Br$, $^{153}SM$, $^{166}Ho$, $^{64}Cu$, $^{121}Pb$, $^{224}Ra$, and $^{223}Ra$. Therefore, the aspect of the present disclosure includes a multispecific antigen binding molecule which is used as an antibody-drug conjugate (ADC) or an antibody-radioisotope conjugate (ARC).

Pharmaceutical Composition and Application Method

The present disclosure further provides a composition. In a preferred embodiment, the composition is a pharmaceutical composition. The pharmaceutical composition comprises the above antibody or active fragments or fusion proteins thereof, or the above multispecific antigen binding molecule, and a pharmaceutically acceptable carrier. Generally, these substances can be prepared in non-toxic, inert and pharmaceutically acceptable water-based carrier media, wherein pH is generally about 5-8, and preferably about 6-8. Although the pH value may be changed along with properties of the prepared substances and to-be-treated diseases, the prepared pharmaceutical composition may be administered by virtue of conventional ways, including (but not limited to): intratumoral, intraperitoneal, intravenous or local administration.

The pharmaceutical composition in the present disclosure can be used for preventing and treating tumors. In addition, other treatment agents may also be simultaneously used.

The pharmaceutical composition in the present disclosure contains the above specific binding molecule (or a conjugate thereof) with a safe and effective dosage (e.g., 0.001-99 wt %, preferably 0.01-90 wt %, and more preferably 0.1-80 wt %) and pharmaceutically acceptable carriers or excipients. The carriers include (but not limited to): brine, buffer solution, glucose, water, glycerin, ethanol or combinations thereof. Pharmaceutical preparations should be matched with an administration manner. The pharmaceutical composition in the present disclosure may be prepared into an injection form, e.g., prepared through a conventional method by using normal saline and an aqueous solution containing glucose and other auxiliary agents. The injection and the solution of the pharmaceutical composition shall be prepared under sterile conditions. A dosage of active ingredients is a therapeutic effective dose, e.g., about 1 microgram/kilogram weight-about 5 milligram/kilogram weight per day. In addition, the polypeptides in the present disclosure may further be used with other therapeutic agent together.

When the pharmaceutical composition is used, an immunoconjugate in a safe and effective dosage is applied to a mammal, wherein the safe and effective dosage is generally at least about 10 microgram/kilogram weight, and does not exceed about 8 milligram/kilogram weight in most instances, and preferably the dosage is about 10 microgram/kilogram weight-about 1 milligram/kilogram weight. Certainly, with respect to a specific dosage, the administration way, a patient health condition and other factors should be considered, which are within in a scope of skills of skilled physicians.

The present disclosure has the following major advantages:

(1) by virtue of massive screening, an anti-CTLA-4 human single-chain antibody fragment (scFv) is obtained in the present disclosure, and the anti-CTLA-4 antibody has the advantages of high affinity and strong specificity;

(2) the recombinant bispecific coupled antibody constructed by using the anti-CTLA-4 single-chain antibody can achieve the effects of enhancing the curative effects of treating Her-2 positive breast cancers by trastuzumab and treating the Her-2 positive breast cancers resistant to the trastuzumab; and (3) the bispecific antibody in the present disclosure can deliver the anti-CTLA-4 antibody scFv into a Her-2 positive tumor region at a fixed point, so that the CTLA-4 antibody enhances immune response in a local region, and any over-reaction of the whole immune system is not caused; and therefore, side effects of the CTLA-4 antibody are reduced.

The present disclosure is further described below in combination with specific embodiments. It can be understood that these embodiments are only used in description of the present disclosure, rather than a limitation of the scope of the present disclosure. Experimental methods without specified detailed conditions in following embodiments are generally performed according to conventional conditions, such as conditions of molecular cloning: laboratory manual (NewYork: Cold Spring Harbor Laboratory Press, 1989) by Sambrook, et al., or according to conditions suggested by manufacturers. Unless additionally defined, percentages and parts are calculated according to the weight. Experimental materials and reagents used in the following embodiments can be commercially available if not specified.

Embodiment 1 Preparation of Anti-CTLA-4 Single-Chain Variable Region (scFv) Antibody A human anti-CTLA-4 single-chain variable region (scFv) antibody is screened by using a phage display library technology.

Specific experimental steps are as follows:

1. Constructing a PIII Phage Display Library 1.1 Preparation of a Humanized cDNA Template Steps: collecting blood of 8 human donors by using blood RNA tubes (PAXgene), and separating peripheral blood mononuclear cell PBMC from the blood (Ficoll Hypaque method); and extracting whole RNA from the PBMC by using RNeasy® Midi Kit (Qiagen), taking the whole RNA as a template, taking oligo(dT) as a primer, and synthesizing a first cDNA strain (SuperScript® III First-Strand Synthesis kit, Invitrogen).

1.2 Amplification of Humanized Antibody Variable Region Genes

Steps: taking the synthesized cDNA as a template, and respectively amplifying antibody heavy chain variable region genes (VH) and light chain variable region genes (VL) by using a polymerase chain reaction (PCR) method.

According to previously published information and the latest V-base sequence directory, PCR primers (literatures) for amplifying the genes VH and VL are designed and GenScript is synthesized. All the PCR reactions are carried out by respectively using a mixed solution of one reverse primer and multiple forward primers. In order to amplify the genes VH, the PCR reaction is carried out between each of the 12 different reverse primers (HVH) and a mixed solution of 4 forward primers (HJH) in a heavy chain J region. VL genes of kappa and lamda types are amplified by using the same method, that is, the PCR reaction is carried out between each of the reverse primers of HVkappa or HVlamda and a mixed solution of corresponding HJkappa or HJlamda. Each PCR reaction has a volume of 100 ul and contains 2 ul of cDNA, respectively 1 uM of the forward primer or reverse primer, 200 uM of dNTPs, 5% of DMSO and 10× of Pfu buffer. After the PCR reaction solution is heated at 94° C. for 5 minutes, 5 units of Pfu(stratagene) are added, and then 30 circular reactions are carried out, wherein each of the circular reactions includes denaturating at 94° C. by 1 minute, annealing at 57° C. by 1 minute and extending at 72° C. by 1 minute. After all the PCR reactions are completed, the PCR reaction solutions for amplifying the genes VH and VL are mixed, agarose gel electrophoresis is performed, and gel purification is performed (QIAquick® Kit, Qiagen).

Steps: respectively connecting the purified genes VH and $V_L$ with a TA vector (Invitrogen), and transforming a connection product into competence XL-1 bacteria (Stratagene) by using an electric shock method (GenePulser Xcell, Bio-Rad); collecting the transformed bacteria in an LB culture medium, totally coating into 10 150-mm LB/Agar culture dishes, and culturing at 37° C. overnight; and scraping the bacteria on the culture dishes to be collected into a 320 ml of LB culture medium, separately filling in 50-ml centrifuge tubes according to an amount of 20 ml per tube, and preserving in a refrigerator at −80° C.

1.3 Construction of the PIII Phage Display Library

Steps: artificially synthesizing a phage vector PIII (GenScript, USA) containing phage coat protein PIII coding genes, wherein polyclonal sites of the vector are located at 5' ends of the PIII genes and are used for cloning antibody variable region genes; and connecting 3' ends of the antibody variable region genes with a His-Tag gene and a restriction enzyme cutting site of enterokinase, so as to purify the scFv antibody;

unfreezing a TA vector library of respectively 20 ml of the VH genes and the VL genes, centrifugally collecting the bacteria, and preparing a plasmid by using a HighPure Midi plasmid purification kit (TianGen); performing double enzyme digestion on the purified plasmid containing the VH genes by using restriction enzymes NcoI-HF and XhoI-HF, and performing double enzyme digestion on the purified plasmid containing the VL genes by using restriction enzymes NheI-HF and NotI-HF, wherein all the restriction enzymes come from New England Biolabs(NEB), and enzyme digestion reactions are carried out at 37° C. overnight; precipitating the enzymatic plasmid with ethanol, dissolving the plasmid in TE buffer, separating the plasmids by using agarose gel electrophoresis, cutting off agarose gel containing the VH or VL gene fragments, and purifying the VH or VL genes (QIAquick® Kit, Qiagen);

cloning the VH genes and the VL genes onto the phage vector PIII in two steps; that is, firstly, performing double enzyme digestion on the phage vector PIII by using the restriction enzymes NheI-HF and NotI-HF, purifying, connecting the purified vector and the purified VL genes by virtue of T4 ligase (NEB), and connecting the VL genes to the 5' end of the coat protein PIII genes, wherein due to the design of primers, the genes are located in the same protein coding framework; transforming the connection product into XL-1 competence bacteria (Stratagene) by using an electric shock method, and culturing the transformed bacteria in 40 150-mm LB/Agar culture dishes, wherein each of the culture dishes contains 2% of glucose, 50 ug/ml of carbenicillin and 20 ug/ml of tetracycline; culturing at 37° C. overnight; scraping the grown bacteria by using a 1600 ml of SB (Super Broth) culture medium, adding 10% of glycerin, separately filling and preserving in a refrigerator at −80° C.; and secondly, cloning the VH genes into the phage vector containing the VL genes, wherein cloning sites NcoI and XhaoI are located at the 5' ends of the VL genes, a connecting peptide coding sequence having 7-15 amino acids exists between the VH genes and the VL genes, and the connection and transformation methods are the same as those of the VL genes; and finally, preparing the humanized scFv phage display library.

2. Screening of Phages Bound with CTLA-4

2.1 Preparation of scFv Expressed Phages

Steps: inoculating the above prepared $5 \times 10^{10}$ bacteria into a 1 L of SB culture medium, wherein the culture medium contains 2% of glucose, 50 ug/ml of carbenicillin and 20 ug/ml of tetracycline; culturing in a shake incubator at 37° C. until cell density OD600 ranges from 0.5 to 0.7; adding helper phages VCSM13 (stratagene) and IPTG having a final concentration of 1 mM of $4 \times 10^{13}$ plaque formation units (PFU); culturing at a room temperature for 30 minutes, diluting to 5 L by using the SB culture medium, and continuously culturing at the room temperature for 2 hours; adding kanamycin having a final concentration of 70 ug/ml, and culturing in a shake incubator at 30° C. overnight; precipitating the bacteria with a centrifugal culture solution, collecting a phage-containing supernatant, transferring into a 500-ml of clean centrifuge tube, adding PEG8000 (Sigma) to reach a final concentration of 4% (w/v) and adding NaCl to reach a final concentration of 3% (w/v), and precipitating the phages; and suspending the phages, and preserving in a PBS (pH of 7.4) containing 2% of BSA.

2.2 Screening of Phages Bound with CTLA-4

Steps: taking a fusion protein (R&D Systems, USA) including an extracellular fragment (amino acids 37-162) of a recombinant human cytotoxic T lymphocyte antigen 4 (CTLA-4) and an IgG constant region as an antigen protein for screening; dissolving the fusion protein CTLA-4/Fv into PBS, adding the fusion protein into an immunoassay tube (Maxisorb, Nunc) under a condition of a concentration of 50 ug/ml, and incubating at a room temperature overnight; closing the immunoassay tube at the room temperature for 1 hour by using 4% of semi-skimmed milk (PBS), adding the above prepared scFv expressed phage having $1 \times 10^{13}$ colony-forming units, and incubating at a room temperature for 2 hours (continuously shaking); cleaning non-bound phages with PBS/0.1% Tween-20, and cleaning with the PBS by 10 times respectively; eluting specifically bound phages at the room temperature with 1 ml of eluant (100 mM NaCl, pH2.2, 0.1% BSA), and neutralizing the eluant with 60 ul of Tris(2M); and repeating the above process twice by using the screened phages, and performing second-round and third-round screening, wherein concentrations of the fusion protein CTLA-4/Fc used in the second-round and third-round screening are respectively 10 ug/ml and 5 ug/ml.

2.3 Monocloning and Gene Sequencing of Positive Phage

Steps: culturing the XL-1 bacteria in the SB culture medium until the OD600 is about 1, adding the positive phages screened in the last round, and continuously culturing in the shake incubator at 37° C. for 1 hour; centrifugally precipitating the bacteria, and culturing the bacteria onto the SB/Agar culture dishes, wherein each of the culture dishes contains 2% of glucose, 50 ug/ml of carbenicillin and 20 ug/ml of tetracycline, and culturing at 30° C. overnight; and selecting single clones on the next day, performing trace plasmid preparation, and performing scFv gene sequencing.

3. Preparation and Analysis of scFv Antibody 3.1 Bacterial Expression and Preparation of the scFv Antibody Steps: subcloning the scFv genes from the obtained monoclonal plasmid to a bacterial expression vector (pET/Flag), and expressing the scFv antibody in BL21/DE3 bacteria and purifying the scFv antibody. See published standard methods for the expression and purification methods.

3.2 ELISA in In-Vitro Binding with CTLA-4

Steps: detecting in-vitro binding ability between the scFv antibody and the CTLA-4 by using an ELISA method (see Embodiment 2 for specific steps); coating an ELISA plate by using a recombinant protein CTLA-4, adding scFv proteins of different concentrations, and detecting quantities of the scFv proteins by using an alkaline phosphatase coupled goat anti-human IgGFab antibody.

In the present embodiment, the human anti-CTLA-4 single-chain variable region (scFv) antibody with excellent specificity and affinity is successfully obtained. After sequenced by a conventional method in the art, sequence information of the antibody is obtained as follows:

In a heavy chain variable region of the human anti-CTLA-4 single-chain variable region (scFv) antibody, each of the FRs and CDRs is as follows:

| | SEQ ID No. | Sequence |
|---|---|---|
| FR1 | 25 | QVQLVQSGGGVVQPGRSLRLSCAASGFTFS |
| CDR1 | 5 | SYGMH |
| FR2 | 26 | WVRQAPGKGLEWVA |
| CDR2 | 6 | VIWYDGSRQYYADS |
| FR3 | 27 | VKGRFTISRDDSKNTMYLQMNSLRAEDTAVYYCAR |

-continued

| SEQ ID No. | Sequence |
|---|---|
| CDR3  7 | GGFWGAFDI |
| FR4   28 | WGQGTMVTVSS |

A sequence of the heavy chain variable region is as follows:

(SEQ ID NO.: 4)
QVQLVQSGGGVVQPGRSLRLSCAASGFTFSSYGMHWVRQAPGKGLEWVA
VIWYDGSRQYYADSVKGRFTISRDDSKNTMYLQMNSLRAEDTAVYYCAR
GGFWGAFDIWGQGTMVTVSS

In a light chain variable region of the human anti-CTLA-4 single-chain variable region (scFv) antibody, each of the FRs and CDRs is as follows:

| | Positions in SEQ ID No.: 12 | Sequence |
|---|---|---|
| FR1' | 29 | DVVMTQSPGTLSLSPGEGATLSC |
| CDR1' | 11 | RASQHVISSYLA |
| FR2' | 30 | WYQQKPGQAPRLLVY |
| CDR2' | 12 | GASSRDT |
| FR3' | 31 | GVSDRFTGSGSGTDFTLTISRLEPED-SAVYFC |
| CDR3' | 13 | QQYGTSPWTF |
| FR4' | 32 | GQGTKLEIKR |

A sequence of the light chain variable region is as follows:

(SEQ ID NO.: 10)
DVVMTQSPGTLSLSPGEGATLSCRASQHVISSYLAWYQQKPGQAPRLLV
YGASSRDTGVSDRFTGSGSGTDFTLTISRLEPEDSAVYFCQQYGTSPWT
FGQGTKLEIKR.

Embodiment 2 Preparation and Detection of Recombinant Bispecific Antibody

A recombinant bispecific coupled antibody having bioactivity is prepared. The antibody has effects of enhancing curative effects of the trastuzumab in treatment of the Her-2 positive tumors and treating the Her-2 positive tumors resistant to the trastuzumab.

FIG. 1 is a structural schematic diagram of the antibody. A gene sequence and a protein sequence of a heavy chain of the antibody are shown in FIG. 2A, and a gene sequence and a protein sequence of a light chain of the antibody are shown in FIG. 2B.

1. Technical Solution 1.1 Construction of Bispecific Coupled Antibody Protein Expression Plasmid Complete cDNA of the heavy chain and the light chain of coded trastuzumab is respectively synthesized by GenScrip (USA) Company. Sequence information of the human anti-CTLA-4 single-chain variable region (scFv) antibody is shown in Embodiment 1, and the antibody is screened by using a phage display library technology.

The inventor discovers that, the vast majority of lysine at C-terminal of the heavy chain of the antibody is degraded in the trastuzumab expression and preparation process, so the lysine is removed when the bispecific coupled antibody is constructed, thereby maintaining completeness of the bispecific coupled antibody.

Heavy chain genes of the Her-2 antibody are amplified by taking synthetic DNA as a substrate by using a polymerase chain reaction (PCR) technology. Sequence information of the Her-2 antibody is as mentioned above. A primer at the 5' end is Her2-F (5'-ATTGAATTCCGCGGCCGCCACCATG-GAG, SEQ ID NO.:33), and a primer at the 3' end is Her2-R (5'-TCCTGGGGACAGTGACAGTG, SEQ ID NO.:34). Anti-CTLA-4 scFv genes are also amplified by the PCR method. A primer at the 5' end is CTLA-Fv-F (5'-CACTGT-CACTGTCCCCAGGACAGGTCCAGCTGGTGCAGTC, SEQ ID NO.:35), and a primer at the 3' end is CTLA-Fv-R (5'-AGAATAGGGCCCTCTAGATTAACGTTT-GATCTCCAGCTTGG, SEQ ID NO.:36). First 20 nucleotide sequences of the primer CTLA-Fv-F are complementary to nucleotide sequences of the primer Her2-R, so that the 2 PRC fragments are connected together in later in-fusion (ClontechLaboratories, Inc.) plasmid cloning. The above two fragments are subjected to DNA gel purification and then mixed with a mammalian cell expression carrier (such as, an expression plasmid containing a CMV promoter) which is subjected to NotI/XbaI double enzyme digestion; and the heavy chain of the Her-2 antibody and the genes of the CTLA-4scFv antibody are connected and cloned into the expression vector by using the in-fusion method.

Light chain cDNA of the antibody is cloned into the same expression vector plasmid by using a subcloning method. Cloning enzymes are NotI and XbaI.

1.2 Establishment of Protein Expression Cell Lines of Antibody

Host cells CHODG44 come from Company Invitrogen. See CHODG44 manual of the company for cell culture and passage methods. Non-transfected cells are subjected to suspension culture in a CDDG44 culture medium (Invitrogen), and the culture medium contains 8 mML-glutamine and 5 ug/ml of recombinant human insulin.

A method for constructing a protein stable expression cell line of the antibody comprises the following steps:

preparing expression vector plasmids of heavy chains and light chains of the antibody by using a TianGen plasmid large-extraction kit, and respectively performing enzyme digestion on 100 ug of DNA of each of the plasmids by using a restriction enzyme PuvI, so as to linearize the plasmids; propagating DG44 cells by at least three generations before the cells are transfected by the expression vector plasmids; taking total 1×10$^7$ DG44 cells, uniformly mixing with the plasmids subjected to enzyme digestion in a 0.8 ml of CDDG44 growth medium, transferring into a 0.4 cm of electric shock cup (Bio-Rad), performing electric shock on a cell/plasmid mixed solution by using an electric transfection instrument (Bio-Rad, GenePulserXcell), culturing the transfected cells in a T-75 cell culture flask, and adding 20 ml of cell growth medium; and placing the T-75 flask containing the transfected cells at 37° C., and culturing in a 8% of CO2 incubator for 24 hours;

culturing the transfected cells for 24 hours, and performing screening culture on the transfected cells in a 96-well culture plate by using a limiting dilution method, wherein a screening culture medium is OptiCHO and contains 8 mML-glutamine, 5 ug/ml of recombinant human insulin and 100 nM of amethopterin (MTX, Sigma); culturing the cells in a 8% of CO2 incubator at 37° C.; after three weeks, analyzing a cell culture solution in each well of which cloned cells are grown by using an ELISA method (an alkaline phosphatase labeled goat anti-human IgGFc antibody, Jackson ImmunoResearch Lab), further amplifying clones with the highest expression, performing ELISA detection, amplifying again, and finally obtaining 12 stable cell lines with the highest expressions; and performing pressurized culture for gradually increasing MTX concentrations on the 12 cell clones, so as to increase expressions of the antibody; totally performing 3 rounds of pressurized culture, wherein each round of the pressurized culture lasts for about 3 weeks; performing antibody expression detection on the 12 clones after the 3 rounds of pressurized culture to obtain 4-5 highly expressed cell lines of the antibody; and screening the monoclonal cell lines on one of the highly expressed cell lines by using a limiting dilution method, and finally obtaining 3-5 highly expressed monoclonal cell lines of the antibody.

1.3 Preparation of Antibody and Identification of Physicochemical Properties

Steps: selecting one highly expressed monoclonal cell line of the antibody, and culturing and amplifying to 2 L; and purifying to prepare an antibody with a culture solution supernatant. A purification method comprises protein-A affinity layer (POROSMabCaptureA, LifeTech), anion chromatography (Q-600C, TOSOH) and cation chromatography (POROSXS, LifeTech).

The purified antibody is subjected to reductive and non-reductive SDS-PAGE electrophoretic analysis and also subjected to HPLC-SEC (high-pressure liquid chromatography-molecular sieve) (TSKgelG3000SWXL, TOSOH) analysis.

1.4 Detection of Binding Between Recombinant Bispecific Coupled Antibody and her-2 on Cell Membrane by Flow Cytometry Steps: performing in vitro incubation on B16 cells (mouse melanoma) subjected to Her-2 stable expressions and recombinant antibodies of different concentrations, taking an appropriate amount of B16/Her-2 positive cells, regulating cell density of the positive cells to be $3\times10^6$/ml with a pre-cooled FACS working solution, separately filling by 100 ul/tube, and closing on ice for 1 hour; diluting the antibodies to different concentrations with the FACS working solution, adding 10 ul of the antibodies of different concentrations into 100 ul of cell suspension, and incubating on ice for 30 minutes; adding 1 ml of FACS working solution into the cell suspension per tube after incubation is completed, performing vortex mixing on the cells to be uniform, centrifuging at a rate of 1200 rpm/min for 5 minutes, removing the supernatant, and repeatedly washing once; diluting an FITC-labeled goat anti-human IgGFc antibody (JacksonImmunoResearchLab) with the FACS working solution, adding 10 ul of the antibody into the cell suspension per tube, enabling the final concentration to be 10 ug/ml, keeping in a dark place, and incubating on ice for 30 minutes; adding 1 ml of FACS working solution into the cell suspension per tube after incubation is completed, performing vortex mixing on the cells to be uniform, centrifuging at the rate of 1200 rpm/min for 5 minutes, removing the supernatant, and repeatedly washing once; and detecting the cells by a flow cytometer C6 (BDBiosciences).

1.5 ELISA Study on Binding Between Recombinant Bispecific Coupled Antibody and CTLA-4

Steps: dissolving a 25 nM of recombinant human CTLA-4-Fc fusion protein (R&DSystems) into a 50 mM of NaHCO$_3$ (pH9.6), adding a 50 ul of CTLA-4 protein into a 96-well ELISA plate, and standing in a refrigerator 4° C. overnight; washing the ELISA plate with PBST (PBS contains 0.05% of Tween-20) on the next day for 3 times, and adding a closing solution of PBST containing 3% of BSA at a dose of 100 ul/well; standing the ELISA plate in an incubator at 37° C. for 1 hour; diluting an antibody protein in a PBST binding solution containing 1% of BSA, and preparing an antibody protein subjected to 3-time serial dilution; pouring the closing solution, adding the antibody protein subjected to 3-time serial dilution at a dose of 50 ul/well, and reacting in the incubator at 37° C. for 1 hour; pouring the antibody protein solution, cleaning the ELISA plate with the PBST for 3 times, adding a second antibody (the alkaline phosphatase labeled goat anti-human IgGFab antibody, JacksonImmunoResearchLab) at a dose of 50 ul/well, and reacting in the incubator at 37° C. for 1 hour; pouring a chromogenic antibody, adding a PBST cleaning solution into the ELISA plate at a dose of 200 ul/well, placing the ELISA plate on a horizontal shaker at a rotation speed of 100 revolutions per minute for 5 minutes, and pouring the cleaning solution; repeating for 5 times, adding an antibody developing solution (PNPP) into the ELISA plate at a dose of 50 ul/well, and placing in the incubator at 37° C.; and reading the plate by a microplate reader at a wavelength of 405 nm.

1.6 Inhibition of In-Vitro Growth of BT-474 Cells of her-2 Positive Breast Cancer Steps: culturing BT-474 cells (purchased from ATCC) in a Dulbecco's Minimum Essential Medium (DMEM) which contains 10% of FBS; digesting the cells with pancreatin and centrifuging, removing the supernatant, suspending the cells in a growth medium, and counting the cells; adding 150 ul of cell suspension containing 10000 cells into each well in a 96-well cell culture plate; culturing in a 5% of CO2 incubator at 37° C. overnight; performing serial dilution on a recombinant antibody or a control antibody by using a growth medium on the next day, and preparing 10 different concentrations; adding 50 ul of the diluted antibody or the control antibody into each well of the cell plate; and culturing the cells for 4 days, adding 20 ul of CCK-8 (a cell proliferation and activity detection kit, DOJINDO) into each well, culturing in a cell incubator for 4 hours, and reading the plate by the microplate reader at 490 nm/655 nm.

1.7 Enhancement of Yield of PHA-Stimulated Human PBMCIL-2

Steps: preparing peripheral blood mononuclear cells (PBMC) from fresh blood of two persons by using an Accuspin (Histopaque-1077, Sigma) method, and suspending the PBMC in an RPMI1640 medium (10% of FBS), so as to reach cell density of $1\times10^6$/ml; adding phytohemagglutinin (PHA) until a final concentration is 1 ug/ml, and culturing the PBMC in a 5% of CO2 incubator at 37° C. for 2 days; washing the PBMC with the PBS once, suspending the cells in the RPMI1640 growth medium, so as to reach cell density of $5\times10^6$/ml; preparing Raji cells (a Chinese cell bank) treated by mitomycin C, suspending the Raji cells in the RPMI1640 growth medium, adding the mitomycin C until the final concentration is 25 ug/ml, incubating at 37° C. for 1 hour, cleaning the cells with the PBS for 4 times, and suspending the cells in the RPMI1640 growth medium, so as to reach cell density of $1\times10^6$/ml; adding the PBMC and the Raji cells with an equivalent volume (50 ul of cells respectively) into each well of the 96-well cell culture plate, and adding an antibody until the final concentration is 10 ug/ml or 30 ug/ml; culturing the cells in the incubator for 72 hours; and collecting the cell culture supernatant, and determining the content of IL-2 in the supernatant by using an ELISA kit (Shanghai ExCell Biological Product Co., Ltd.).

1.8 Enhancement of Immune Response of Monkey on HBsAg Antigen

CTLA-4 may be bound in an scFv region of a bispecific antibody in the present disclosure. A co-stimulatory inhibiting effect of the CTLA-4 on T cells CD28 is blocked, and immune response of the immune system is further enhanced. Since the humanized anti-CTLA-4 antibody scFv may be bound with CTLA-4 of a cynomolgus monkey, influences of the bispecific antibody in the present disclosure on the immune response in a body of the cynomolgus monkey on a recombinant hepatitis B vaccine HBsAg (GSK, Engerix B) are detected by using the cynomolgus monkey.

Steps: dividing 8 cynomolgus monkeys (at an age of 2-3) into 2 groups, wherein each group contains 2 female cynomolgus monkeys and 2 male cynomolgus monkeys; performing intravenous injection on monkeys in a control group with humanized IgG1 on the $1^{st}$ day and the $29^{th}$ day, and performing intravenous injection on monkeys in a test group with the bispecific antibody, wherein an injected dose is 10 mg of antibody for each kilogram of the monkeys, and an antibody protein concentration is 5 mg/ml; performing intramuscular injection on each of the monkeys with bug of the recombinant hepatitis B vaccine on the $2^{nd}$ day and the $30^{th}$ day; and taking blood from each of the monkeys to prepare plasma on the $35^{th}$ day and the $49^{th}$ day, and determining HBsAg antibody titers in the plasma by using the ELISA method.

Due to too many samples, a mean titer of the antibodies in the plasma in the same group of the monkeys is detected at first. The brief method includes the following steps: diluting the HBsAg protein to 2 ug/ml by using a coating buffer (200 mM NaHCO3, pH9.6), adding 50 ul into each well of the 96-well ELISA plate, and standing in a refrigerator at 4° C. overnight; washing the ELISA plate with PBST (PBS contains 0.05% of Tween-20) on the next day for 3 times, and adding a closing solution of PBST containing 3% of BSA at a dose of 100 ul/well, and placing the ELISA plate in an incubator at 37° C. for 1 hour; taking partial plasma, performing equivalent volume mixing on the plasma in the same group on the same day, and diluting the mixed plasma by 100 times, 500 times, 2500 times and 12500 times with a binding solution (PBST contains 1% of BSA); pouring the closing solution after closing of the ELISA plate is completed, adding a diluted plasma mixed solution at a dose of 50 ul/well, and incubating in the incubator at 37° C. for 2 hours; pouring the plasma solution, cleaning the ELISA plate with the PBST for 3 times, adding a second antibody (the alkaline phosphatase labeled goat anti-monkey IgGFc antibody, Abcam, item No. of ab112765) diluted by 2000 times at a dose of 50 ul/well, and reacting in the incubator at 37° C. for 2 hours; pouring the second antibody, adding a PBST cleaning solution into the ELISA plate at a dose of 200 ul/well, placing the ELISA plate on a horizontal shaker at a rotation speed of 100 revolutions per minute for 5 minutes, pouring the cleaning solution, and repeating the cleaning process for 5 times; adding an antibody developing substrate PNP solution (Southern Biotech, China) into the ELISA plate at a dose of 50 ul/well, and placing in the incubator at 37° C.; and reading the plate by a microplate reader (Bio-Rad) at a wavelength of 405 nm.

It is indicated from the above experimental results that, the best ELISA results can be obtained from the plasma sample diluted by 1000 times. The anti-HBsAg antibody titer of each monkey is detected by using the same ELISA method, the plasma of each of the monkeys is diluted by 1000 times, and the rest steps are the same as those in the above method. In order to conveniently compare the content of the HBsAg antibody of each of the monkeys, an antibody unit in the mixed plasma from the monkeys in the experimental group on the $49^{th}$ day is set as 5000 units/ml. The mixed plasma is taken as a standard to perform serial dilution, and the ELISA is performed. Then, the content of the HBsAg antibody of each of the monkeys is calculated, and two parallel points are formed in each of the samples.

2. Implementation Effects

2.1 Preparation, Purification and Identification of Bispecific Antibody

Figure 3:
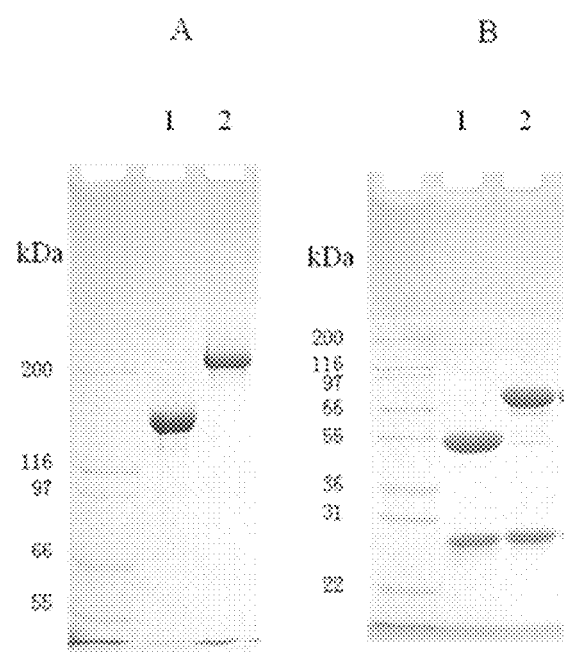
FIG. 3 shows SDS-PAGE electrophoretic analysis of a bispecific coupled antibody; A: non-reductive 6% SDS-PAGE electrophoretic analysis, 3 ug/sample; B: reductive 10% SDS-PAGE electrophoretic analysis, 5 ug/sample; Lane 1) represents human IgG1 antibody, and lane 2) represents bispecific coupled antibody; A lane on the leftmost side is a protein molecular weight standard (kDa)

The bispecific antibody is purified by a Protein-A affinity column, an anion column and a cation column, and analyzed by reductive and non-reductive SDS-PAGE electrophoresis gel (FIG. 3). FIG. 3A shows that a molecular weight of the complete bispecific antibody is about greater than 200 kDa and is very close to a theoretical value 196 kDa. The reductive SDS-PAGE electrophoresis gel shows that a heavy chain molecular weight of the bispecific antibody is 75-80 kDa and is consistent with a theoretical molecular weight (74.4 kDa).

Figure 4:
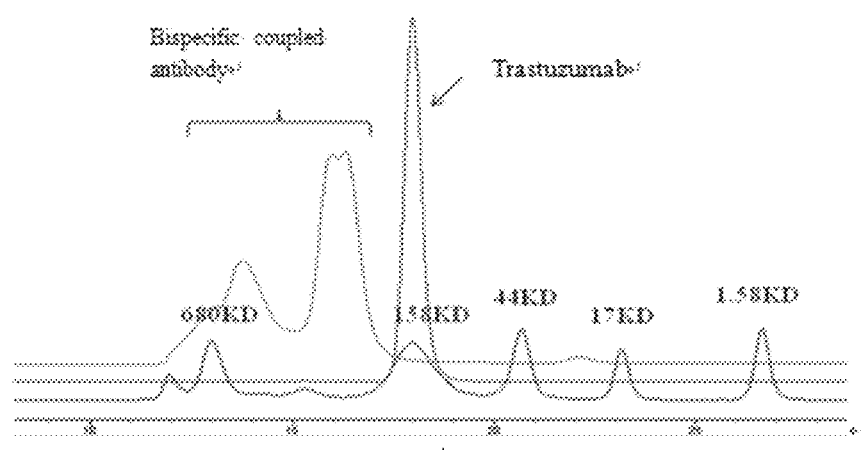
FIG. 4 shows a bispecific coupled antibody subjected to HPLC-SEC analysis and purification. The bispecific coupled antibody is purified by using a Protein-A affinity column and then passes through an anion chromatography column, and breakthrough liquid is separated by a cation-exchange column; blue represents a protein molecular weight standard, a red line represents a peak map of a trastuzumab monoclonal antibody, and a green peak is the bispecific coupled antibody.

The bispecific antibody analyzed and purified by the HPLC-SEC shows that 40% of the purified antibodies may be dimmers, and the rest 60% of the antibodies are monomers (FIG. 4).

2.2 Binding Between Bispecific Antibody and Cell Membrane her-2

Figure 5:
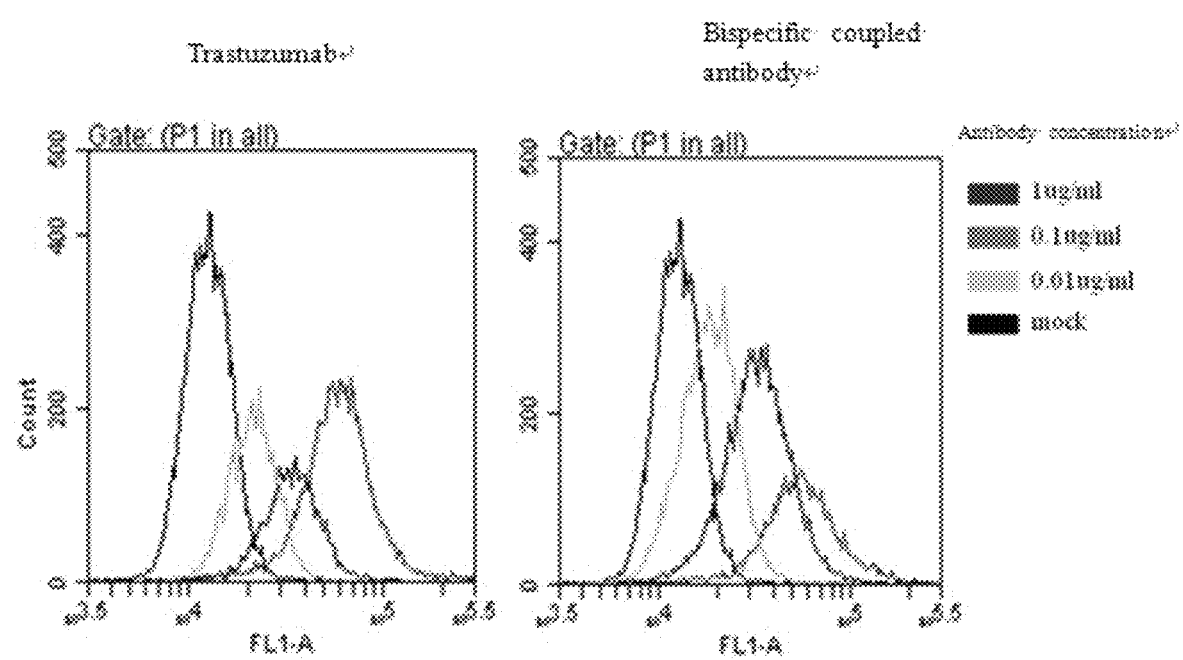
FIG. 5 shows analysis of binding of a bispecific coupled antibody and a cytomembrane Her-2 by flow cytometry. After mouse melanoma cells (B16) subjected to Her-2 stable transfection are incubated in antibodies of different concentrations, an antibody bound with the Her-2 is detected by using an FITC-labeled goat anti-human IgG1Fc antibody, and FITC fluorescence intensity is detected by flow cytometry; Mock is an antibody-free experimental group.

The binding ability of the bispecific antibody with Her-2 on a cell membrane is detected by flow cytometry. Trastuzumab and the Her-2 on the cell membrane are contrasted. FIG. 5 shows that the two antibodies bound with the Her-2 have similar fluorescence intensity, which indicates that the bispecific antibody has the same binding ability with the Her-2 on the cell membrane as the trastuzumab.

2.3 In-Vitro Binding Between Bispecific Antibody and CTLA-4

Figure 6:
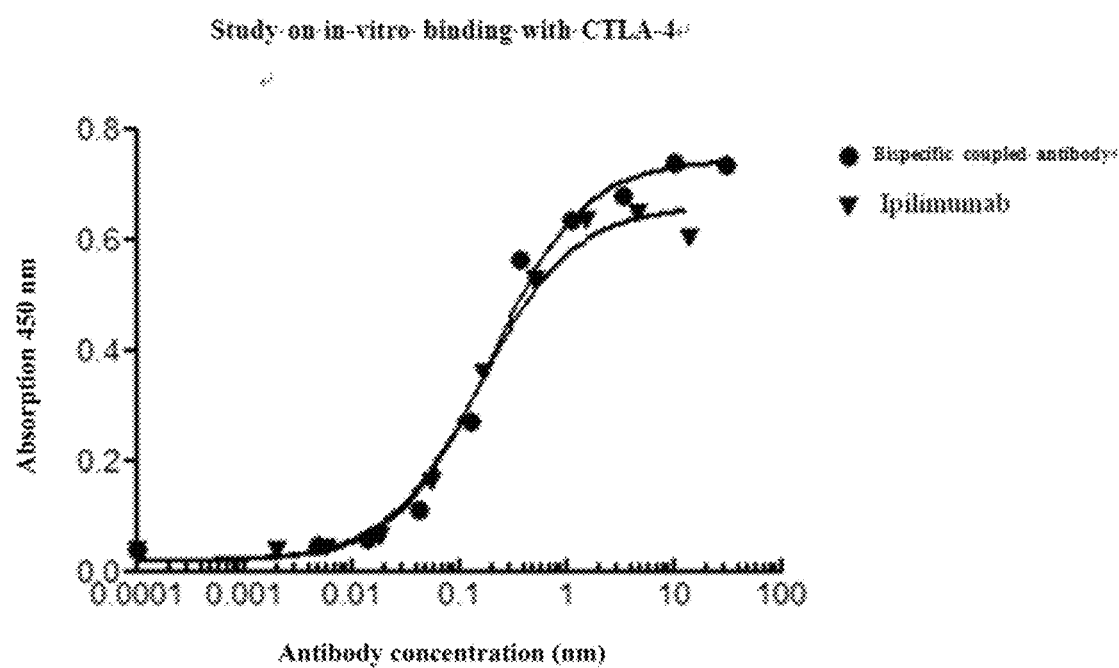
FIG. 6 shows analysis of in-vitro binding between a bispecific coupled antibody and CTLA-4 by ELISA; a recombinant human CTLA-4-Fc fusion protein is coated in a 96-well ELISA plate, an antibody bound with CTLA-4-Fc is detected by a goat anti-human IgG1Fc antibody, and the goat anti-human IgG1Fc antibody is labeled by alkaline phosphatase.

Affinity binding ability of the bispecific antibody with CTLA-4 is detected by using an ELISA method. The bispecific antibody can be specifically bound with the CTLA-4, has EC50 of 0.19 nM, and is similar to binding ability with Ipilimumab (EC50 is 0.16 nM) (FIG. 6).

2.4 Inhibition of Growth of BT-474 Cells by Bispecific Antibody

Figure 7:
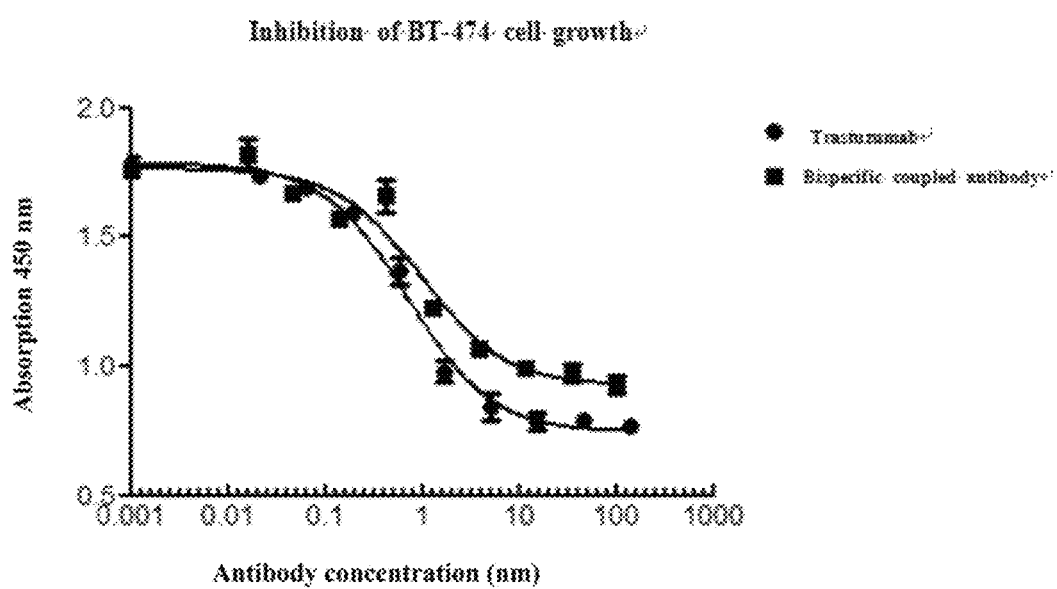
FIG. 7 shows a growth inhibition study of Her-2 positive tumor cells, and BT-474 cells and antibodies of different concentrations are co-cultured for 4 days and then detected.

The trastuzumab can inhibit in-vitro growth of BT-474 cells of Her-2 positive breast cancers. Therefore, ability of the bispecific antibody for inhibiting growth of the BT-474 cells is detected (FIG. 7). Research results prove that the bispecific antibody can well inhibit the growth of the BT-474 cells. IC50 of the bispecific antibody is 0.97 nm and is close to that of the trastuzumab (0.69 nM). A purpose of this experiment is to prove that anti-Her-2 regions of the bispecific antibody in the present disclosure have ability of inhibiting the growth of the BT-474 cells. Since the bispecific antibody in the present disclosure is coupled by two antibodies, the two antibodies may be influenced with each other, e.g., formation of an accurate space structure of the other party or binding between the other party and a corresponding antigen is influenced. This experiment proves that antigen binding units included in the bispecific antibody in the present disclosure still reserve respective activities.

2.5 Enhancement of IL-2 Expression of PBMC by Bispecific Antibody

Figure 8:
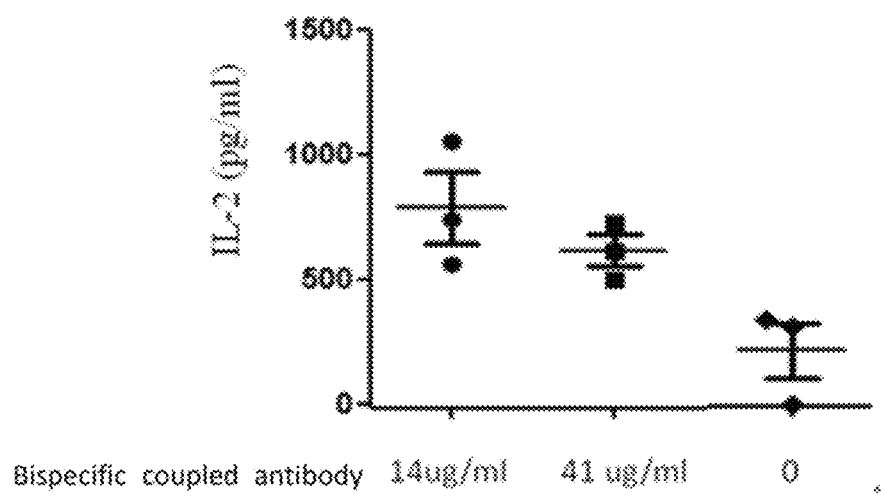
FIG. 8 shows a method for expressing IL-2 by activation-enhanced PBMC, separating the PBMC from 2 human donors, activating with PHA, co-culturing with Raji cells and a bispecific antibody for 72 hours, centrifugally precipitating the cells, collecting supernatant, and determining content of the IL-2 in the supernatant by an ELISA method.

After the CTLA-4 antibody is bound with the CTLA-4, a negative regulator signal of the CTLA-4 to activation of T cells is blocked. Therefore, an activation state of the T cells is maintained or enhanced, and expressions of various interleukins, including IL-2, are increased. The inventor tests influences of the bispecific antibody on PHA-activated human PBMCIL-2 expressions, and discovers that the bispecific antibody can obviously increase IL-2 expressions of the PBMC (FIG. 8, increased by about 2 times compared with a control group) compared with an experimental group without an antibody. The result proves that the bispecific antibody can maintain or enhance the activation state of the T cells.

Figure 9:
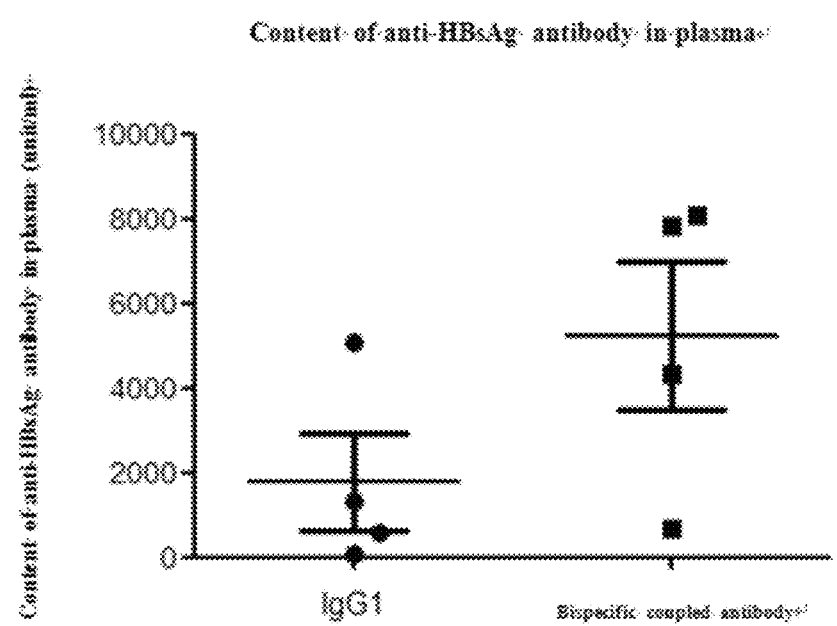
FIG. 9 shows a method for injecting HBsAg vaccine and a bispecific antibody or content of the HBsAg antibody in monkey plasma with IgG1 proteins in a control group; detecting the antibody content by an ELISA method, coating an HBsAg protein in a 96-well ELISA plate, incubating with plasma diluted by 1000 times, and detecting an antibody bound with the HBsAg by using an alkaline phosphatase-labeled goat anti-monkey IgG Fc antibody.

2.6 Enhancement of Immune Response of Cynomolgus Monkeys on HBsAg by Bispecific Antibody A mean titer of anti-HBsAg antibodies in plasma of cynomolgus monkeys injected with vaccines within the $49^{th}$ day is detected by using the ELISA method. Results show that plasma antibody titers of the monkeys injected with the vaccines are close to 10000 times (without data display). The content of the anti-HBsAg antibodies of each of the monkeys is detected by using the same method. After injected with the vaccines within the $7^{th}$ week, only 2 of the 4 monkeys in the experimental group have antibody content of 8000 units/ml; 1 monkey has an antibody content close to 5000 units/ml, and the last monkey has an antibody content of 700 units/ml only. With respect to the 4 monkeys in the control group, 3 monkeys have an antibody content close to 1500 units/ml or lower than 1000 units/ml, and only 1 monkey has an antibody content of 5000 units/ml (FIG. 9). By comparing the antibody content of the 2 groups of the monkeys, results show that the bispecific antibody in the present disclosure has the function of enhancing the immune response caused by the vaccines in vivo.

All literatures mentioned in the present disclosure should be taken as references in the present application, just as each of the literatures is independently quoted as a reference. In addition, it should be understood that, those skilled in the art may make various changes or modifications to the present disclosure under the teaching of above description. These equivalent forms are also included in a scope limited by claims in the present application.

We claim:

1. A multispecific antigen binding molecule comprising:
a first antigen binding domain (D1); and
a second antigen binding domain (D2),
wherein the D1 specifically binds to a target molecule Her-2 protein;
the D2 specifically binds to a target molecule CTLA-4 protein;
the D1 is an antibody or an antibody fragment which specifically binds to the Her-2 protein; and
the D2 is an antibody or an antibody fragment which specifically binds to the CTLA-4 protein;
the D2 has a heavy chain variable region shown in SEQ ID NO: 4 and a light chain variable region shown in SEQ ID NO: 10.

2. An anti-CTLA-4 antibody, comprising: a heavy chain variable region and a light chain variable region; the heavy chain variable region comprises three complementary determining regions (CDRs) CDR as follows:
CDR1 shown in SEQ ID NO: 5,
CDR2 shown in SEQ ID NO: 6, and
CDR3 shown in SEQ ID NO: 7;
the light chain variable region comprises three CDRs as follows:
CDR1 shown in SEQ ID NO: 11,
CDR2 shown in SEQ ID NO: 12, and
CDR3 shown in SEQ ID NO: 13.

3. A recombinant protein, comprising: the antibody of claim 2 and optionally a tag sequence for assisting expression and/or purification.

4. The anti-CTLA-4 antibody according to claim 2, wherein the heavy chain variable region has the amino acid sequence shown in SEQ ID NO: 4.

5. The anti-CTLA-4 antibody according to claim 2, wherein the light chain variable region has the amino acid sequence shown in SEQ ID NO: 10.

* * * * *